United States Patent
Nebuya

(10) Patent No.: US 10,357,179 B2
(45) Date of Patent: Jul. 23, 2019

(54) LENGTH MEASUREMENT DEVICE, LENGTH MEASUREMENT METHOD, PROGRAM, SHAPE ESTIMATION DEVICE, AND BODY FAT PERCENTAGE MEASUREMENT DEVICE

(71) Applicant: SCHOOL JURIDICAL PERSON KITASATO INSTITUTE, Tokyo (JP)

(72) Inventor: Satoru Nebuya, Sagamihara (JP)

(73) Assignee: SCHOOL JURIDICAL PERSON KITASATO INSTITUTE, Tokyo (JP)

( * ) Notice: Subject to any disclaimer, the term of this patent is extended or adjusted under 35 U.S.C. 154(b) by 468 days.

(21) Appl. No.: 15/025,615

(22) PCT Filed: Sep. 19, 2014

(86) PCT No.: PCT/JP2014/074854
§ 371 (c)(1),
(2) Date: Mar. 29, 2016

(87) PCT Pub. No.: WO2015/046058
PCT Pub. Date: Apr. 2, 2015

(65) Prior Publication Data
US 2016/0235334 A1 Aug. 18, 2016

(30) Foreign Application Priority Data

Sep. 30, 2013 (JP) .................................. 2013-204223

(51) Int. Cl.
*A61B 5/053* (2006.01)
*G01B 3/10* (2006.01)
(Continued)

(52) U.S. Cl.
CPC ............ *A61B 5/0537* (2013.01); *A61B 5/053* (2013.01); *A61B 5/1072* (2013.01);
(Continued)

(58) Field of Classification Search
CPC ..... A61B 5/053; A61B 5/0537; A61B 5/1077; A61B 5/1072; G01B 7/02; G01B 7/293
See application file for complete search history.

(56) References Cited

U.S. PATENT DOCUMENTS

| | | | |
|---|---|---|---|
| 6,597,955 B2 * | 7/2003 | Panescu ............... | A61B 5/0422 606/41 |
| 2005/0099278 A1 | 5/2005 | Kawaura et al. | |

(Continued)

FOREIGN PATENT DOCUMENTS

| | | |
|---|---|---|
| EP | 3 017 758 | 5/2016 |
| JP | 60-067804 | 4/1985 |

(Continued)

OTHER PUBLICATIONS

Beck, et al., Effects of muscle-to-electrode distance on the human diaphragm electromyogram, 1995, American Physiological Society, p. 975-984.*

(Continued)

*Primary Examiner* — Daniel L Cerioni
*Assistant Examiner* — Raymond P Dulman
(74) *Attorney, Agent, or Firm* — Nixon & Vanderhye P.C.

(57) ABSTRACT

A length measurement device includes a tape portion (10) which is provided with a plurality of electrode pads (100a, 100b, 101a, 1010b, . . . ) arrayed thereon and is used in a state being wound around a measuring object, an impedance acquisition unit that selects any pair of electrode pads from a plurality of electrode pads and acquires electrical impedance between the pair of electrode pads, and a length calculation unit that calculates a length between the pair of electrode pads, based on a change in impedance of the pair of electrode pads.

10 Claims, 17 Drawing Sheets

(51) Int. Cl.
  *G01B 7/02* (2006.01)
  *A61B 5/107* (2006.01)
  *G01B 7/293* (2006.01)
(52) U.S. Cl.
  CPC .............. *A61B 5/1077* (2013.01); *G01B 3/10* (2013.01); *G01B 7/02* (2013.01); *G01B 7/293* (2013.01); *A61B 2560/0468* (2013.01); *A61B 2562/0209* (2013.01); *A61B 2562/043* (2013.01); *A61B 2562/125* (2013.01); *A61B 2562/164* (2013.01); *A61B 2562/182* (2013.01)

(56) References Cited

U.S. PATENT DOCUMENTS

| | | | | |
|---|---|---|---|---|
| 2005/0124909 | A1* | 6/2005 | Kasahara | A01K 29/00 600/547 |
| 2007/0288064 | A1* | 12/2007 | Butson | A61B 5/0538 607/45 |
| 2011/0025348 | A1* | 2/2011 | Chetham | A61B 5/053 324/649 |
| 2011/0034912 | A1* | 2/2011 | de Graff | H01L 27/14687 606/21 |
| 2011/0050256 | A1 | 3/2011 | Frangen | |
| 2011/0264000 | A1* | 10/2011 | Paul | A61B 5/0537 600/547 |
| 2011/0288605 | A1* | 11/2011 | Kaib | A61B 5/0006 607/5 |
| 2011/0295096 | A1* | 12/2011 | Bibian | A61B 5/0478 600/372 |
| 2011/0295144 | A1* | 12/2011 | Murakawa | A61B 5/0537 600/547 |
| 2011/0309400 | A1 | 12/2011 | Fukushima et al. | |
| 2012/0172747 | A1* | 7/2012 | Fukuda | A61B 5/0537 600/547 |
| 2012/0198715 | A1* | 8/2012 | Eaton | A61B 5/1077 33/512 |
| 2012/0277619 | A1* | 11/2012 | Starkebaum | A61B 5/053 600/547 |
| 2013/0035606 | A1* | 2/2013 | Wichner | A61B 5/7203 600/546 |
| 2013/0172720 | A1* | 7/2013 | Yamamori | A61B 5/053 600/382 |

FOREIGN PATENT DOCUMENTS

| | | |
|---|---|---|
| JP | 11-113870 | 4/1999 |
| JP | 2005-140700 | 6/2005 |
| JP | 2005-253610 | 9/2005 |
| JP | 2005-345107 | 12/2005 |
| JP | 2010-205988 | 9/2010 |
| JP | 2011-053212 | 3/2011 |
| JP | 2011-240775 | 12/2011 |

OTHER PUBLICATIONS

Extended European Search Resort issued in Appln. No. 14849148.3 dated Apr. 7, 2017.
International Search Report for PCT/JP2014/074854 dated Nov. 11, 2014, 2 pages.
Written Opinion of the ISA for PCT/JP2014/074854 dated Nov. 11, 2014, 4 pages.

* cited by examiner

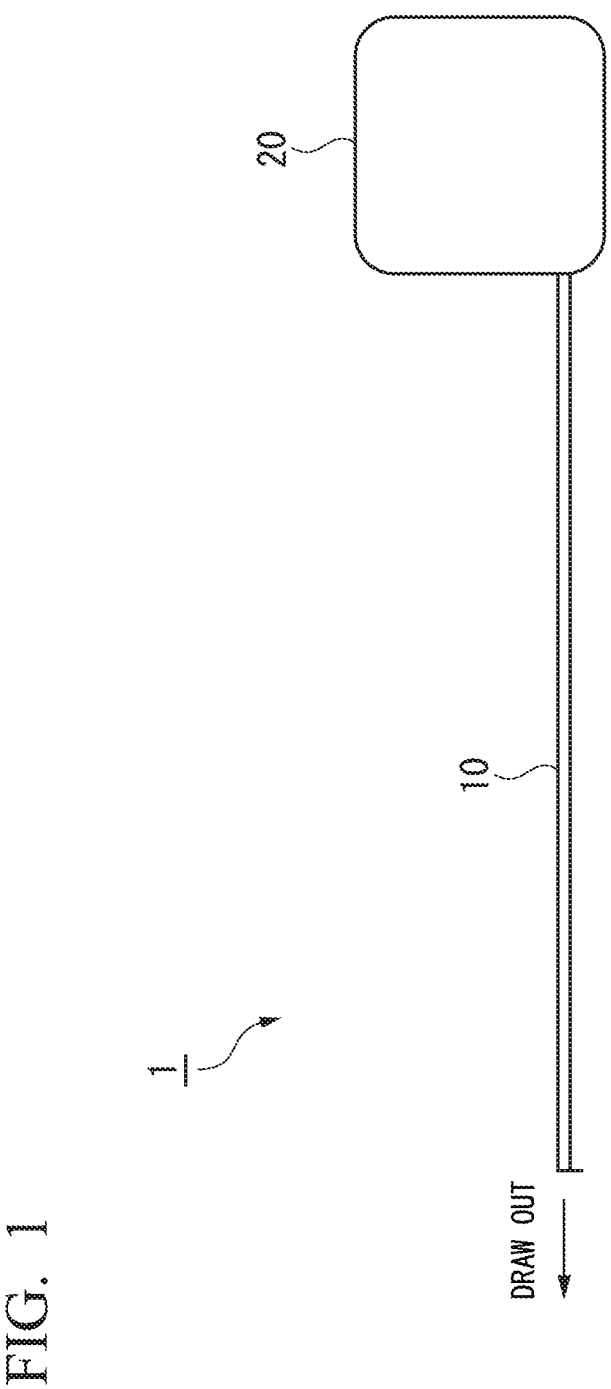

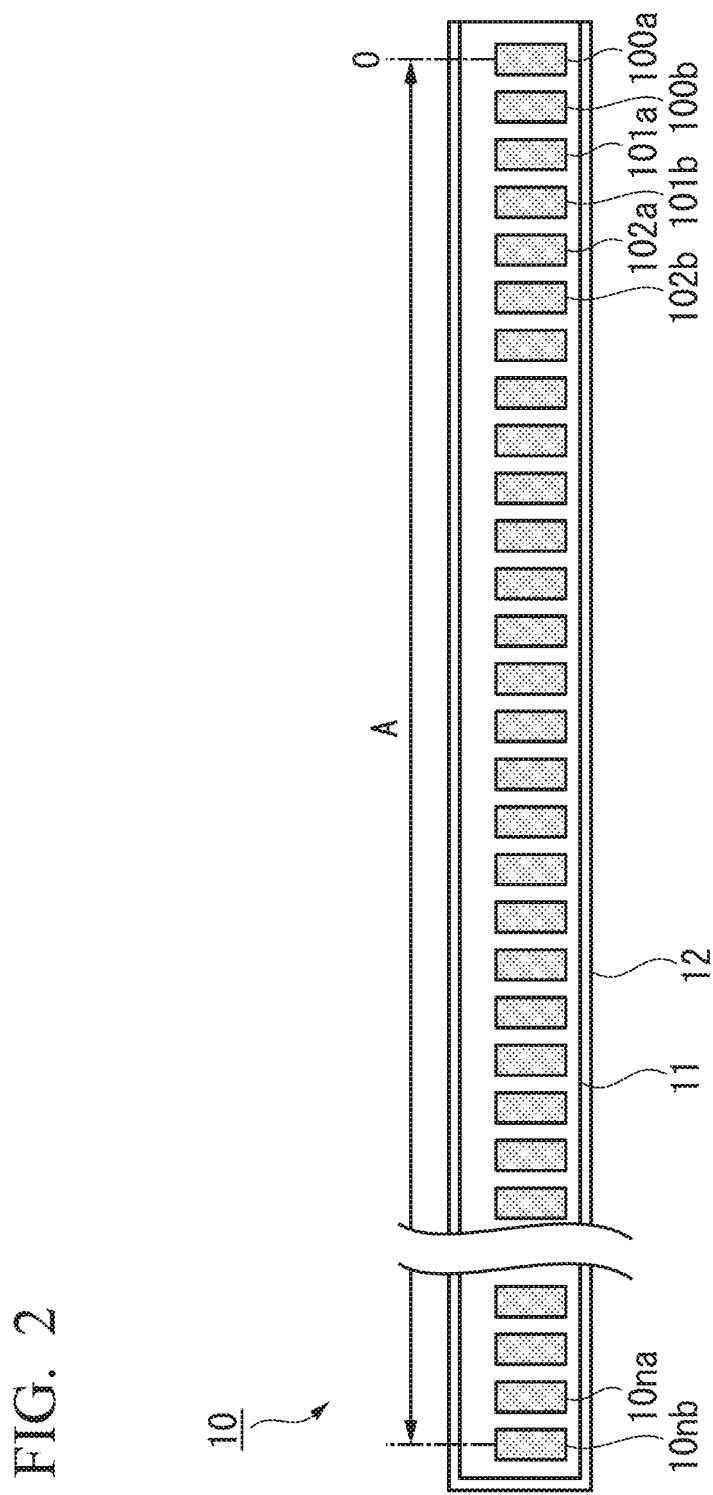

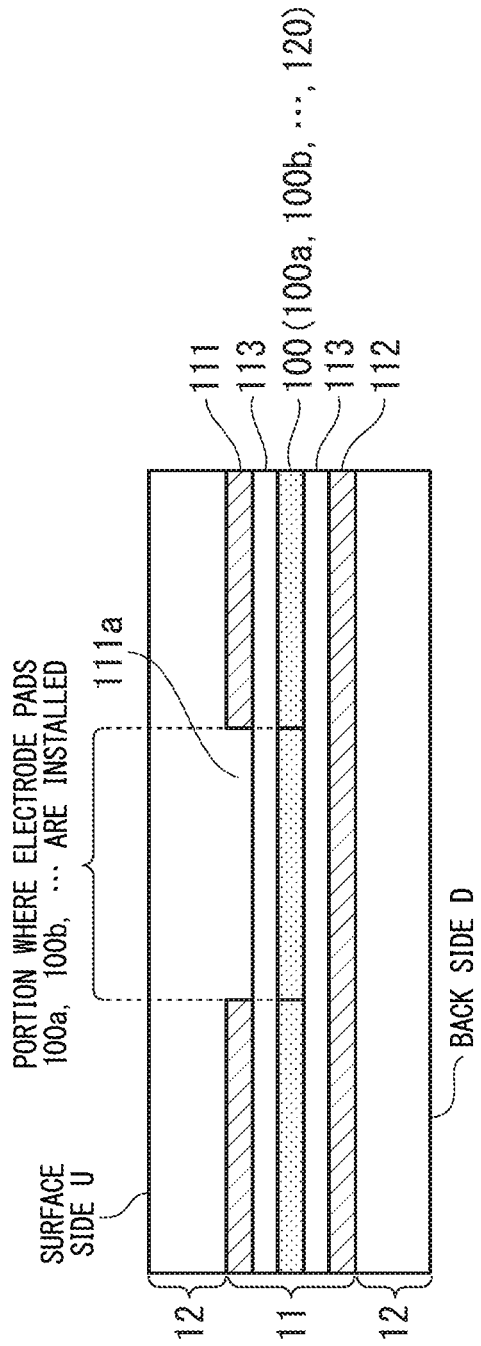

LENGTH MEASUREMENT DEVICE, LENGTH MEASUREMENT METHOD, PROGRAM, SHAPE ESTIMATION DEVICE, AND BODY FAT PERCENTAGE MEASUREMENT DEVICE

TECHNICAL FIELD

The present invention relates to a length measurement device that measures a length of a measuring object, a length measurement method, a program, a shape estimation device, and a body fat percentage measurement device.

This application is the U.S. national phase of International Application No. PCT/JP2014/074854, filed Sep. 19, 2014 which designated the U.S. and claims priority to Japanese Patent Application No. 2013-204223, filed Sep. 30, 2013, the entire contents of which are incorporated herein by reference.

BACKGROUND ART

In recent years, there has been progress in the development of an electronic measure, with the progress of a reduction in the size of electronic parts (see, for example, PTL 1). The electronic measure disclosed in PTL 1 is configured to draw out a tape portion from a main unit in the same manner as those of normal measures, and acquires the length of the tape portion drawn out from the main unit, using a sensor included in the main unit. According to such an electronic measure, a user can easily ascertain the length of a measuring object without reading gradations given to the tape portion with respect to the measuring object.

CITATION LIST

Patent Literature

[PTL 1] Japanese Unexamined Patent Application, First Publication No. 2005-345107

SUMMARY OF INVENTION

Technical Problem

However, for example, when the tape portion is drawn out from the main unit or is housed (wound) into the main unit at the time of measuring the length of a measuring object, the aforementioned electronic measure is configured to detect the length of the drawn-out or housed tape portion using an optical sensor. For this reason, a user needs to perform a process of drawing out the tape portion or housing the tape portion into the main unit at the time of length measurement. In addition, in order to accurately measure the length of a measuring object, the tape portion is required to be drawn out while one side of the measuring object is arranged at a reference point given to the tape portion in advance, which leads to a large burden of a user's measurement work.

The present invention provides a length measurement device, a length measurement method, a program, a shape estimation device, and a body fat percentage measurement device which are capable of reducing a user's burden during the measurement of a length.

Solution to Problem

According to a first aspect of the present invention, there is provided a length measurement device including a tape portion provided with a plurality of electrode pads arrayed thereon and which is used in a state being wound around a measuring object, an impedance acquisition unit that selects any pair of electrode pads from the plurality of electrode pads and acquires electrical impedance between the pair of electrode pads, and a length calculation unit that calculates a length between the pair of electrode pads, based on a change in impedance of the pair of electrode pads.

According to a second aspect of the present invention, the above-described length measurement device further includes a positional relationship data storage unit that stores positional relationship data indicating a positional relationship between the plurality of electrode pads, and the length calculation unit calculates the length between the pair of electrode pads, using the positional relationship data.

According to a third aspect of the present invention, in the above-described length measurement device, the tape portion is formed by arraying the plurality of electrode pads on a flexible substrate.

According to a fourth aspect of the present invention, in the above-described length measurement device, the plurality of electrode pads are arrayed along a longitudinal direction of the tape portion, the impedance acquisition unit selects a plurality of the pairs of electrode pads and acquires electrical impedance therebetween for each of the pairs of electrode pads, and the length calculation unit identifies an area of the tape portion in which a pair of electrode pads having the electrical impedance set to be below a determination threshold are arrayed, and calculates a length of the identified area.

According to a fifth aspect of the present invention, in the above-described length measurement device, the impedance acquisition unit performs a first acquiring step of selecting a plurality of pairs of electrode pads arrayed at a first separation distance and acquiring electrical impedance therebetween for each of the plurality of pairs of electrode pads, and a second acquiring step of selecting a plurality of pairs of electrode pads arrayed at a second separation distance larger than the first separation distance and acquiring electrical impedance therebetween for each of the plurality of pairs of electrode pads.

According to a sixth aspect of the present invention, in the above-described length measurement device, in a case where a plurality of proximity areas which are areas of the tape portion having the electrical impedance, acquired in the first acquiring step, set to be below the determination threshold exist with a non-proximity area which is an area exceeding the determination threshold interposed therebetween, the length calculation unit determines whether the electrical impedance acquired in the second acquiring step is below the determination threshold in the non-proximity area, and calculates a length of an entire area in which the plurality of proximity areas exist in a case where the electrical impedance is set to be below the determination threshold.

According to a seventh aspect of the present invention, in the above-described length measurement device, the tape portion is coated by a coated portion of which a surface is formed of an insulator.

According to an eighth aspect of the present invention, in the above-described length measurement device, the tape portion further includes a shield portion constituted by a conductor formed inside the coated portion so as to cover any one surface of the plurality of electrode pads and both surfaces of a routing wiring connected to the electrode pad.

According to a ninth aspect of the present invention, in the above-described length measurement device, the tape portion is configured such that the electrode pad and the routing wiring connected thereto are formed of a conductive fiber.

According to a tenth aspect of the present invention, in the above-described length measurement device, the tape portion further includes a shape estimation unit that has a plurality of curvature sensors arrayed along a longitudinal direction, and estimates a shape of an area of the tape portion which is wound around the measuring object, based on a radius of curvature which is detected by the plurality of curvature sensors.

According to an eleventh aspect of the present invention, in the above-described length measurement device, each of the plurality of curvature sensors is provided integrally with each of the plurality of electrode pads.

According to a twelfth aspect of the present invention, the above-described length measurement device further includes a body fat percentage calculation unit that calculates a body fat percentage of a living body around which the tape portion is wound, based on the electrical impedance acquired by the impedance acquisition unit.

According to a thirteenth aspect of the present invention, there is provided a length measurement method using a length measurement device including a tape portion which is provided with a plurality of electrode pads periodically arrayed along a longitudinal direction and is used in a state being wound around a measuring object, the method including causing an impedance acquisition unit to select a plurality of pairs of electrode pads from the plurality of electrode pads and acquire electrical impedance therebetween for each of the plurality of pairs of electrode pads, and causing a length calculation unit to identify an area of the tape portion in which a pair of electrode pads having the electrical impedance set to be below a determination threshold are arrayed, and calculate a length of the identified area.

According to a fourteenth aspect of the present invention, there is provided a program causing a computer of a length measurement device, including a tape portion which is provided with a plurality of electrode pads periodically arrayed along a longitudinal direction and is used in a state being wound around a measuring object, to function as impedance acquisition device of selecting a plurality of pairs of electrode pads from the plurality of electrode pads and acquiring electrical impedance therebetween for each of the plurality of pairs of electrode pads, and length calculation device of identifying an area of the tape portion in which a pair of electrode pads having the electrical impedance set to be below a determination threshold are arrayed, and calculating a length of the identified area.

According to a fifteenth aspect of the present invention, there is provided a shape estimation device including a tape portion which is provided with a plurality of curvature sensors arrayed along a longitudinal direction and is used in a state being wound around a measuring object, and a shape estimation unit that estimates a shape of an area of the tape portion which is wound around the measuring object, based on a radius of curvature which is detected by the plurality of curvature sensors.

According to a sixteenth aspect of the present invention, there is provided a body fat percentage measurement device including a tape portion which is provided with a plurality of electrode pads periodically arrayed along a longitudinal direction and is used in a state being wound around a living body, an impedance acquisition unit that selects a plurality of pairs of electrode pads from the plurality of electrode pads and acquires electrical impedance therebetween for each of the plurality of pairs of electrode pads, and a body fat percentage calculation unit that calculates a body fat percentage of the living body around which the tape portion is wound, based on the electrical impedance acquired by the impedance acquisition unit.

Advantageous Effects of Invention

It is possible to reduce a user's burden during the measurement of a length.

BRIEF DESCRIPTION OF DRAWINGS

FIG. 1 is a diagram illustrating an outline of a length measurement device according to a first embodiment.

FIG. 2 is a diagram illustrating a configuration of a tape portion of the length measurement device according to the first embodiment.

FIG. 3B is a second diagram illustrating a configuration of the tape portion of the length measurement device according to the first embodiment in more detail.

DESCRIPTION OF EMBODIMENTS

First Embodiment

Figure 3A:
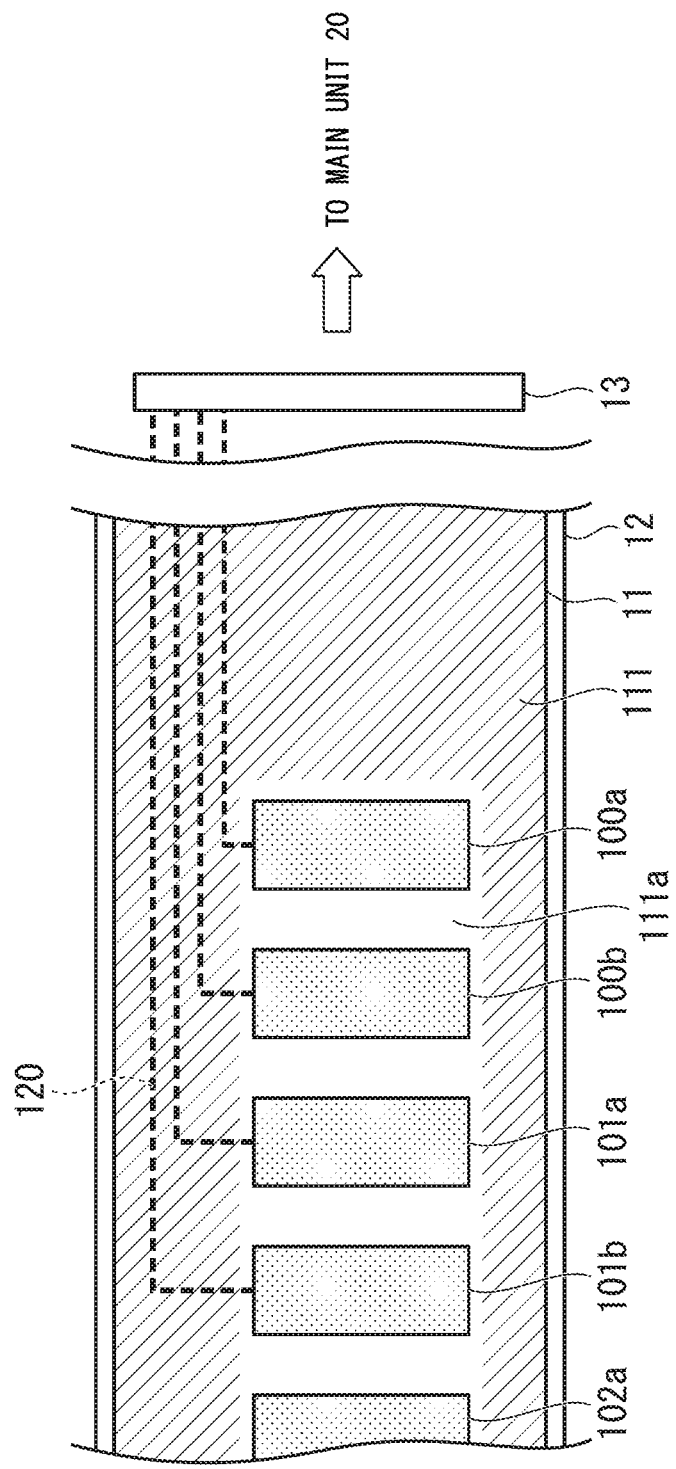
FIG. 3A is a first diagram illustrating a configuration of the tape portion of the length measurement device according to the first embodiment in more detail.

Hereinafter, a length measurement device according to a first embodiment will be described with reference to the accompanying drawings.

FIG. 1 is a diagram illustrating an outline of the length measurement device according to the first embodiment.

As shown in FIG. 1, a length measurement device 1 includes a tape portion 10 and a main unit 20. Similarly to a normal measure, the length measurement device 1 is configured such that the tape portion 10 is formed of a flexible material and is housed inside the main unit 20 in a state of being wound around a reel. A user of the length measurement device 1 draws out the tape portion 10 from the main unit 20, and winds this tape portion around a measuring object to thereby measure the length of the measuring object.

FIG. 2 is a diagram illustrating a configuration of the tape portion of the length measurement device according to the first embodiment.

Next, the configuration of the tape portion 10 will be described with reference to FIG. 2.

As shown in FIG. 2, the tape portion 10 is constituted by a flexible substrate 11 and a coated portion 12.

The flexible substrate 11 has a plurality of electrode pads 100a, 100b, 101a, 101b, . . . , 10na, and 10nb (n is an integer of 1 or greater) periodically arrayed along the longitudinal direction thereof. The electrode pads 100a, 100b, . . . are all formed on the flexible substrate 11 at equal intervals (for example, intervals of 1 millimeter).

The flexible substrate 11 is formed of a resin material which is flexible in shape and has electrical insulating properties. The electrode pads 100a, 100b, . . . and routing wirings 120 (shown in FIGS. 3A and 3B described later) of the tape portion 10 are fabricated by patterning a conductive film formed on the flexible substrate 11.

In the following description, the position A of each of the electrode pads 100a, 100b, . . . on the tape portion 10 is described by a separation distance from a reference point O (position of the electrode pad 100a) to each of the electrode pads 100a, 100b, 101a, . . . .

As described later, the electrode pads 100a, 101a, . . . are used as anode terminals to which an alternating-current voltage signal for electrical impedance measurement is applied. In addition, the electrode pads 100b, 101b, . . . are used as cathode terminals to which a ground potential is given.

The coated portion 12 is formed of an insulator such as a resin or a fiber, and coats the entire surface of the flexible substrate 11 including each of the electrode pads 100a, 100b, . . . . In this manner, the electrode pads 100a, 100b, . . . are not exposed to the outside by the coated portion 12 coating the entirety of the flexible substrate 11. Thereby, it is possible to prevent the electrode pads from rusting or being altered, or to reduce a failure due to an electrostatic breakdown through each of the electrode pads 100a, 100b . . . .

FIGS. 3A and 3B are a first diagram and a second diagram, respectively, illustrating a configuration of the tape portion of the length measurement device according to the first embodiment in more detail.

FIG. 3A shows a part of front view of the tape portion 10. As shown in FIG. 3A, the flexible substrate 11 has the routing wirings 120 included therein. Each of the routing wirings 120 is formed, for example, in the same layer as that in which each of the electrode pads 100a, 100b, . . . is formed. One side of the routing wiring is connected to each of the electrode pads 100a, 100b . . . , and the other side thereof is connected to the main unit 20 (electrode selecting unit 25 (FIG. 4) described later) through a connector 13. As described later, the main unit 20 sends out a high-frequency signal to each of the electrode pads 100a, 100b, . . . through the connector 13 and the routing wiring 120.

FIG. 3B shows a schematic cross-sectional view of the tape portion 10. As shown in FIG. 3B, the flexible substrate 11 has a structure in which a signal wiring portion 100 which is a conductor layer having the electrode pads 100a, 100b, . . . and the routing wirings 120 formed therein and shield portions 111 and 112 which are other layers are laminated in a multilayer manner with an insulating layer 113 interposed therebetween. Here, the shield portions 111 and 112 are conductor layers formed of a conductor, similarly to the signal wiring portion 100 in which the electrode pads 100a, 100b . . . and the like are formed. In addition, each of the shield portions 111 and 112 is grounded in the main unit 20, and is fixed to a ground potential.

Meanwhile, FIG. 3B shows a schematic cross-sectional view of the tape portion 10 in a state where the "surface side U" and the "back side D" of the tape portion 10 are identified, but the length measurement device 1 in the present embodiment measures the length of a measuring object by causing the object to face the "surface side U" of the tape portion 10.

As shown in FIG. 3B, the shield portions 111 and 112 are formed on the "surface side U" and the "back side D" shown in FIG. 3B, respectively, with respect to the signal wiring portion 100 with the insulating layer 113 interposed therebetween. That is, the signal wiring portion 100 is arrayed within the flexible substrate 11 so as to be interposed between the shield portions 111 and 112 from the "surface side U" and the "back side D".

As shown in FIGS. 3A and 3B, the shield portion 111 which is laminated on the "surface side U" of the signal wiring portion 100 has intermittent portions 111a formed in areas facing the surfaces of the electrode pads 100a, 100b, . . . . Thereby, the facing surfaces of the electrode pads 100a, 100b, . . . are not covered with the shield portion 111. That is, as shown in FIG. 3A, the shield portion 111 covers portions other than areas in which the facing surfaces of the electrode pads 100a, 100b . . . of the signal wiring portion 100 exist, particularly, areas in which the routing wirings 120 are arrayed.

On the other hand, the shield portion 112 is formed so as to cover the entire surface of the "back side D" of the signal wiring portion 100 without having intermittent portions.

As described above, the shield portions 111 and 112 are formed inside the coated portion 12 so as to cover any one surface (surface on the "surface side U") of the electrode pads 100a, 100b, . . . and both surfaces of the routing wirings 120 connected to the electrode pads 100a, 100b, . . . (FIGS. 3A and 3B). Thereby, since areas (the entirety of both surfaces of the routing wirings 120) other than the facing surfaces of the electrode pads 100a, 100b, . . . with respect to a measuring object are covered with the shield portions 111 and 112, it is possible to reduce an influence of electromagnetic interference from the outside during measurement, and to perform measurement having a minimal error.

Figure 4:
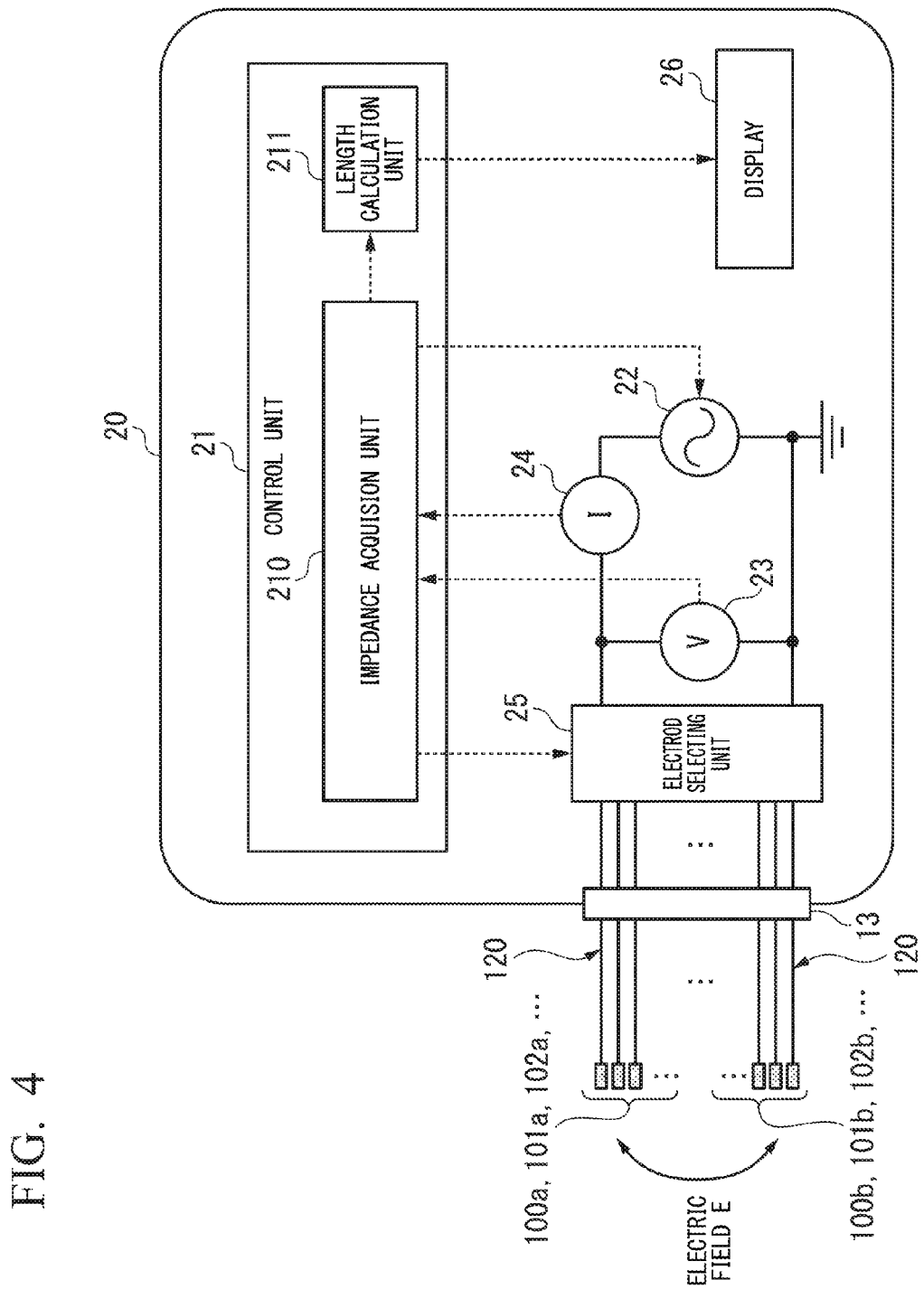
FIG. 4 is a diagram illustrating functional components of a main unit of the length measurement device according to the first embodiment.

FIG. 4 is a diagram illustrating functional components of the main unit of the length measurement device according to the first embodiment.

Next, each functional component of the main unit 20 will be described in detail with reference to FIG. 4. Meanwhile, in FIG. 4, wirings of a circuit which link respective function units are shown by a solid line, and flows of signals (information) between the respective function units are shown by a broken line.

As shown in FIG. 4, the main unit 20 includes a control unit 21, an oscillation source 22, a voltmeter 23, an ammeter 24, an electrode selecting unit 25, and a display 26.

The control unit 21 is a central process unit (CPU) that takes charge of the entire process of the length measurement device 1, and has a function as an impedance acquisition unit 210 and a length calculation unit 211. The specific functions of the impedance acquisition unit 210 and the length calculation unit 211 will be described later.

The oscillation source 22 is configured such that one terminal is connected to a reference potential (ground potential) point, and that the other terminal outputs an alternating-current voltage signal of a predetermined frequency based on a ground potential. The oscillation source 22 receives a control signal of the control unit 21 (impedance acquisition unit 210), and outputs an alternating-current voltage signal.

The voltmeter 23 and the ammeter 24 acquire a voltage value and a current value, respectively, on a circuit shown in FIG. 4, and output the acquired values to the control unit 21 (impedance acquisition unit 210). The voltmeter 23 and the ammeter 24 may be analog/digital (A/D) converters that acquire a voltage and a current which are detected, as voltage information and current information (sampling value).

The electrode selecting unit 25 is a relay switch that changes the connection of the wirings of the circuit in accordance with a control signal which is supplied from the control unit 21 (impedance acquisition unit 210). Specifically, the electrode selecting unit 25 selects any one of the routing wirings 120 connected to the electrode pads 100a, 101a, 102a, . . . , as an electrode pad on the anode side, and connects the selected one to ("the other terminal" of) the oscillation source 22 through the connector 13. Further, the electrode selecting unit 25 selects any one of the routing wirings 120 connected to the electrode pads 100b, 101b, 102b, . . . , as an electrode pad on the cathode side, and connects the selected one to the ground potential point.

The display 26 displays length information based on the length information (information indicating a measurement result of a length) supplied from the control unit 21 (length calculation unit 211), and causes a user to visually recognize the length information. The display 26 is constituted by, for example, a simplified liquid crystal display or the like.

Next, the functions of the impedance acquisition unit 210 and the length calculation unit 211 which are included in the control unit 21 will be described.

The impedance acquisition unit 210 selects a plurality of two electrode pads (pair of electrode pads) from a plurality of electrode pads 100a, 100b, . . . , and acquires electrical impedance therebetween for each of the plurality of pairs of electrode pads.

Specifically, the impedance acquisition unit 210 outputs a control signal to the above-described oscillation source 22, outputs an alternating-current voltage signal of a predetermined frequency (for example, order of several MHz to several hundred MHz), and acquires electrical impedance based on the voltage information and the current information which are acquired through the voltmeter 23 and the ammeter 24. In this case, the impedance acquisition unit 210 also outputs a control signal to the electrode selecting unit 25, and selects two of the electrode pads 100a, 100b, . . . . For example, the electrode selecting unit 25 selects the electrode pad 100a and the electrode pad 100b based on the control signal of the impedance acquisition unit 210, and connects these electrode pads. Then, the impedance acquisition unit 210 acquires electrical impedance between the two electrode pads 100a and the electrode pad 100b.

The impedance acquisition unit 210 acquires electrical impedance between one pair of electrode pads (for example, the electrode pad 100a and the electrode pad 100b), and temporarily stores and holds the electrical impedance. The impedance acquisition unit 210 selects another pair of electrode pads (for example, the electrode pad 100b and the electrode pad 101a), and acquires electrical impedance therebetween. The impedance acquisition unit 210 repeats such a process, and acquires electrical impedance between a pair of electrode pads over the entire range of the tape portion 10.

Meanwhile, a specific process flow of the impedance acquisition unit 210 (control unit 21) will be described in detail with reference to a flow diagram (FIG. 7) described later.

Meanwhile, the circuit configured in the above-described main unit 20 is an example, and the present embodiment is not limited to the circuit as shown in FIG. 4. For example, the circuit shown in FIG. 4 may be configured such that various elements (such as resistive elements and capacitors) for impedance matching, and amplifiers or filters for improving the accuracy of detection are appropriately arrayed.

In addition, a description has been given of a case where the above-described impedance acquisition unit 210 acquires the electrical impedance between a pair of electrode pads based on the voltage information and the current information which are acquired through the voltmeter 23 and the ammeter 24, but a length measurement device 1 according to a modified example of the present embodiment is not limited to such an aspect. For example, the impedance acquisition unit 210 of the length measurement device 1 according to the modified example may detect a reflection component based on mismatching of output impedance from the oscillation source 22, and may acquire electrical impedance based thereon. Additionally, any aspect may be used insofar as electrical impedance between electrodes can be acquired in the aspect.

The length calculation unit 211 refers to a series of electrical impedances (FIG. 6 described later) acquired by the impedance acquisition unit 210, identifies an area of the tape portion 10 in which a pair of electrode pads having the electrical impedance set to be below a predetermined determination threshold are arrayed, and calculates the length of the identified area. In addition, the length calculation unit 211 performs a process of outputting information (length information) indicating the calculated length to the display 26.

The specific processing details of the length calculation unit 211 will be described later.

Figure 5A:
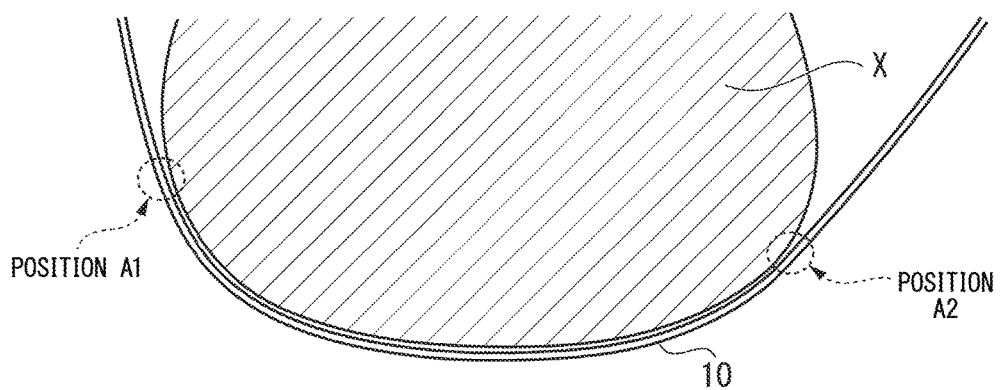
FIG. 5A is a first diagram illustrating an action of the length measurement device according to the first embodiment.
Figure 5B:
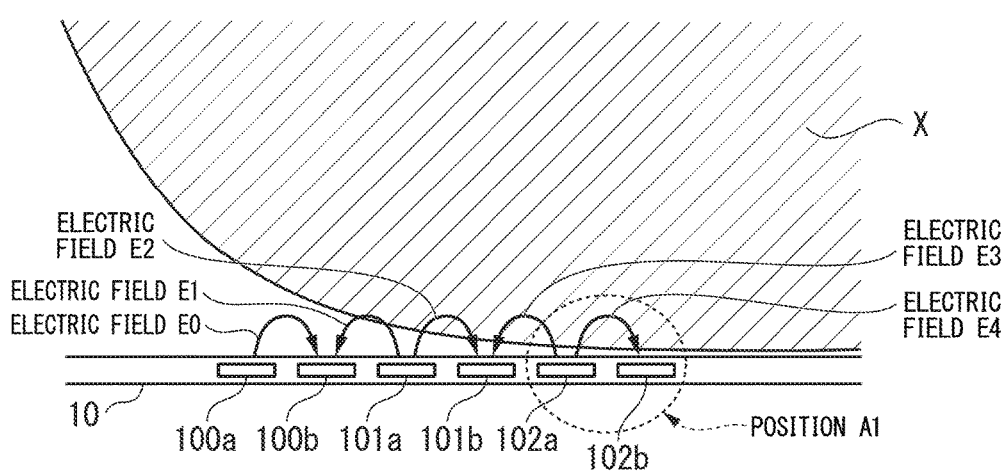
FIG. 5B is a second diagram illustrating an action of the length measurement device according to the first embodiment.

FIGS. 5A and 5B are a first diagram and a second diagram, respectively, illustrating an action of the length measurement device according to the first embodiment.

FIG. 5A shows a state where the tape portion 10 is arrayed so as to be partially wound around a measuring object X.

As shown in FIG. 5A, a case will be described in which the tape portion 10 is arrayed from a position A1 to a position A2 along the periphery of the measuring object X which is a living body. The tape portion 10 is in proximity of the measuring object X in the area from the position A1 to the position A2, and is separated from the measuring object X in other areas.

FIG. 5B is a diagram particularly illustrating the vicinity of the position A1 of the tape portion 10 in a state shown in FIG. 5A.

For example, the electrode pads 100a, 100b, 101a, 101b, 102a, and 102b are arrayed in the vicinity of the position A1 as shown in FIG. 5B. In this case, based on a process flow (described later) of measurement, the impedance acquisition unit 210 acquires, for example, electrical impedances between the electrode pads 100a and 100b, between the electrode pads 101a and 100b, between the electrode pads 101a and 101b, . . . , and electrical impedances between each of the pairs of electrode pads while changing the pairs of electrode pads in order. The electrical impedances which are acquired by the impedance acquisition unit 210 are values dependent on electric fields E0, E1, . . . , and E4 (FIG. 5B) which are generated between each of the pairs of electrode pads.

Here, attention is focused on paths of the electric fields E0 to E4 which are generated between each of the pairs of electrode pads. As shown in FIG. 5B, the electrode pads 100a and 100b are not in proximity of the measuring object X, and the electric field E0 generated therebetween is generated in the atmosphere. On the other hand, the electrode pads 102a and 102b are in proximity of the measuring object X at the position A1, and thus the electric field E4 which is generated therebetween passes through the measuring object X (living body). Therefore, the electrical impedance between the electrode pads 102a and 102b is measured to be lower than the electrical impedance between the electrode pads 100a and 100b.

That is, since the electrode pads 100a, 100b, . . . come close to the measuring object X gradually toward the position A1, the electric fields E0, E1, E2, E3, and E4 increase in the number of areas passing through the measuring object X gradually in the paths thereof. Therefore, the electrical impedance corresponding to each of the electric fields E0 to E4 decreases gradually.

In this manner, in an area where the tape portion 10 is in proximity to the measuring object X, the electrical impedance between a pair of electrode pads within the area is measured to be low. In an area where the tape portion 10 is not in proximity to the measuring object X, the electrical impedance between a pair of electrode pads within the area is measured to be high.

Figure 6:
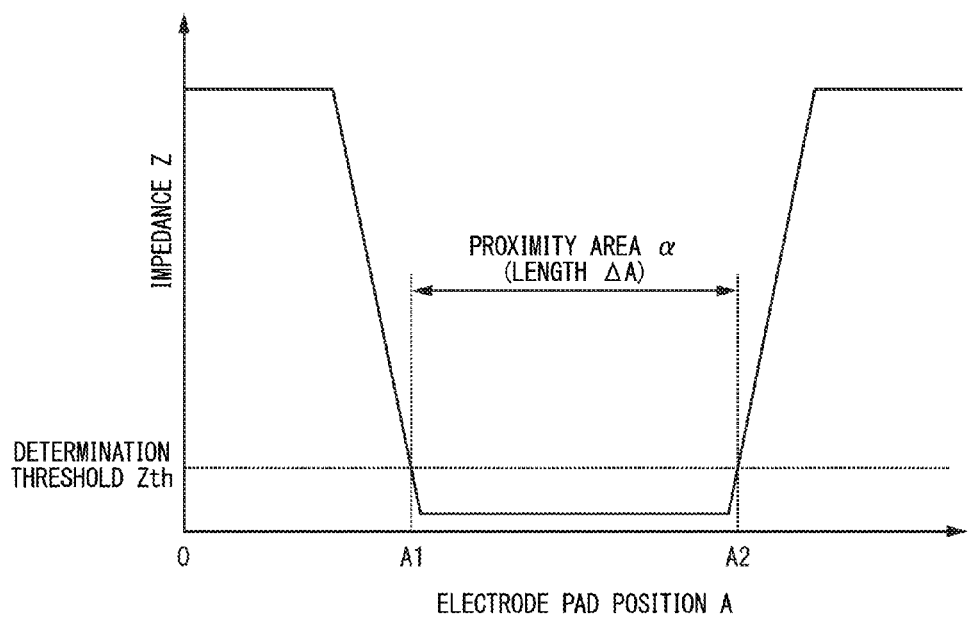
FIG. 6 is a third diagram illustrating an action of the length measurement device according to the first embodiment.

FIG. 6 is a third diagram illustrating an action of the length measurement device according to the first embodiment.

In a graph shown in FIG. 6, the horizontal axis represents a position A of the tape portion 10, and the vertical axis represents electrical impedance Z between a pair of electrodes which are arrayed at the position A.

As described with reference to FIGS. 5A and 5B, a tendency is exhibited in which the electrical impedance Z which is acquired by the impedance acquisition unit 210 decreases between a pair of electrode pads belonging to an area which is in proximity of the measuring object X, and increases between a pair of electrode pads belonging to an area which is not in proximity of the object.

Therefore, in the states shown in FIGS. 5A and 5B, the electrical impedance Z which is acquired by the impedance acquisition unit 210 is acquired as the graph shown in FIG. 6. That is, the electrical impedance Z decreases gradually with the vicinity of the position A1 of the tape portion 10 as a boundary, and an area where low electrical impedance Z is acquired continues in the area (position A1 to position A2) which is in proximity of the measuring object X. After the position A2 from which an area separated from the measuring object X again starts, high impedance Z is acquired again.

Here, as described above, the length calculation unit 211 refers to a series of electrical impedances (FIG. 6) acquired by the impedance acquisition unit 210, identifies an area of the tape portion 10 in which a pair of electrode pads having the electrical impedance Z set to be below a predetermined determination threshold Zth are arrayed, and calculates the length of the identified area.

Specifically, the length calculation unit 211 previously stores the determination threshold Zth for performing a determination process. As shown in FIG. 6, the area (proximity area α (FIG. 6)) is identified where the electrical impedance Z which is set to be below the determination threshold Zth is acquired. Here, the length calculation unit 211 stores each of the electrode pads 100a, 100b, . . . and each of the positions A arrayed on the tape portion 10 in association with each other. Specifically, the length calculation unit 211 includes a positional relationship data storage unit (not shown) in which an identifier allocated for each of the electrode pads 100a, 100b, . . . and a position (distance from a predetermined reference point) on the tape portion 10 having each of the electrode pads 100a, 100b, . . . disposed thereon are previously stored in association with each other.

Thereby, the length calculation unit 211 can detect, for example, that the electrical impedance Z between the electrode pads 102a and 102b is set to be below the determination threshold Zth, and determine that the position A1 on the tape portion 10 corresponding to these electrode pads 102a and 102b is a position to which the measuring object X is in proximity.

In this manner, when the length calculation unit 211 identifies the proximity area α in which the electrical impedance Z is set to be below the determination threshold on the tape portion 10, the length calculation unit next calculates a length ΔA of the proximity area α. Specifically, the length calculation unit 211 calculates the length ΔA of the proximity area α based on the calculation of ΔA=A2−A1.

Figure 7:
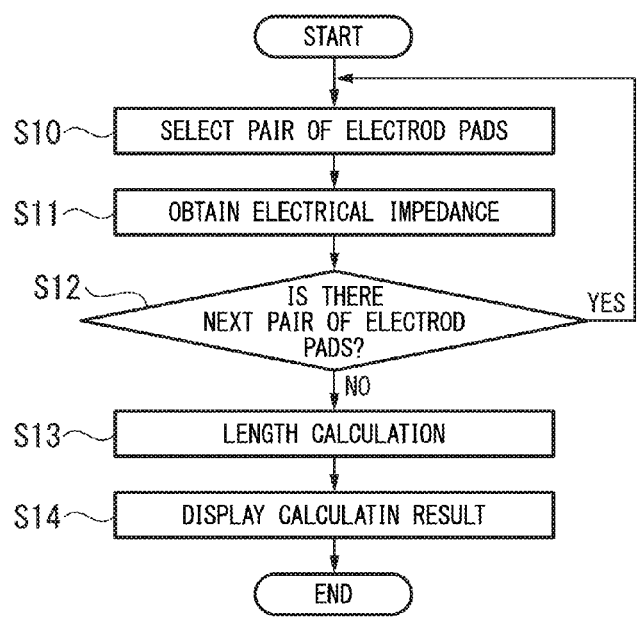
FIG. 7 is a diagram illustrating a process flow of a control unit of the length measurement device according to the first embodiment.

FIG. 7 is a diagram illustrating a process flow of the control unit of the length measurement device according to the first embodiment.

The process flow of the control unit 21 having the functions described above will be described in order with reference to FIG. 7.

The process flow of the control unit 21 shown in FIG. 7 starts immediately after an operation in a state where a user can use the length measurement device 1 is performed (for example, immediately after a main power is on).

First, the impedance acquisition unit 210 of the control unit 21 selects two of the electrode pads 100a, 100b, . . . periodically arrayed on the tape portion 10 in which the electrical impedance Z attempts to be acquired (step S10). Here, the impedance acquisition unit 210 outputs a predetermined control signal to the electrode selecting unit 25, to thereby control the electrode selecting unit 25. The electrode selecting unit 25 performs a wiring connection process according to the control signal, and selects a desired pair of electrode pads.

Here, for example, the impedance acquisition unit 210 selects two electrode pads 100a and 100b.

Next, the impedance acquisition unit 210 acquires the electrical impedance Z between the selected electrode pads 100a and 100b (step S11). Here, the impedance acquisition unit 210 first outputs a control signal for measurement start to the oscillation source 22. The oscillation source 22 outputs an alternating-current voltage signal of a predetermined frequency, based on the control signal for measurement start. This alternating-current voltage signal is transmitted through a medium between the electrode pads 100a and 100b, and is detected by the voltmeter 23 and the ammeter 24. The impedance acquisition unit 210 takes in the voltage information and the current information which are detected by the voltmeter 23 and the ammeter 24, and acquires electrical impedance.

Next, the impedance acquisition unit 210 determines whether the next pair of electrode pads is selected (step S12).

For example, when the electrode pads 100a and 100b are selected in step S10, the impedance acquisition unit 210 determines that there is the next electrode pad (step S12: YES), and selects the next pair of electrode pads (electrode pads 100b and 101a) in step S10.

The impedance acquisition unit 210 repeats the processes of steps S10 to S12, and acquires electrical impedances between the pairs of electrode pads 100a, 100b, . . . which are adjacent to each other in order from the reference point O of the tape portion 10. The process of acquiring electrical impedance finishes at a point in time when the electrical impedance between the electrode pads 10na and 10nb on the end is acquired (step S12: NO).

When the processes (steps S10 to S12) of the impedance acquisition unit 210 acquiring electrical impedance finish, the length calculation unit 211 of the control unit 21 refers to the acquired electrical impedances, and performs a process of calculating the length ΔA (step S13). Specifically, as described above, the determination threshold Zth and the electrical impedance Z are compared with each other, and the proximity area α in which the electrical impedance Z is set to be below the determination threshold Zth is identified (see FIG. 6). The length ΔA of the proximity area α which is an area in proximity of the measuring object X is then calculated.

Meanwhile, in step S13, the length calculation unit 211 may calculate the length ΔA only in a case where the proximity area α in which the electrical impedance Z is set to be below the determination threshold Zth exists, and may not perform the process of calculating the length ΔA in a case where no area on the tape portion 12 is set to be below the determination threshold Zth.

The length calculation unit 211 outputs length information indicating the calculated length ΔA to the display 26, displays a calculation result (measurement result of the length) (step S14), and finishes the measurement process. Thereby, a user can ascertain the length of the measuring object X (area between the positions A1 and A2).

The control unit 21 of the length measurement device 1 may stand by for a certain period of time after the finish of step S14, and then return to step S10 to periodically repeat a series of measurement processes of steps S10 to S14. Thereby, since results of the latest length measurement are constantly updated and displayed on the display 26, the convenience of a user is improved.

In addition, the control unit 21 may perform a series of measurement processes of steps S10 to S14, based on the detection of pressing down of a "measurement start button" which is separately provided in the main unit 20. In this manner, it is possible to start length measurement at a user's desired timing (timing of pressing down of the measurement start button). Further, in this case, when the measurement of the length is completed, a user may be caused to recognize that effect by outputting an electronic sound.

Next, the effects of the length measurement device 1 according to the above-described first embodiment will be described.

According to the length measurement device 1 of the present embodiment, the control unit 21 automatically calculates the length of the area which is in proximity of the measuring object X, based on the comparison of the determination threshold with the electrical impedance between each of the pairs of electrode pads of the electrode pads 100a, 100b, . . . provided on the tape portion 10. Here, in a case of a normal measure, for example, work is required, such as the winding of the tape portion on the chest followed by the reading and subtraction of gradations of intersecting portions. On the other hand, according to the length measurement device 1 of the present embodiment, a user can ascertain the length (ΔA) of the wound and contacted portion merely by winding the tape portion 10 on the measuring object X. Thereby, it is possible to simply measure even the bodies of users who have difficulty in moving their bodies, such as, for example, an elderly person or a care-receiving person.

In addition, in a case where measurement is performed on his or her own body using the normal measure, it may be difficult for a person to read gradations alone depending on measurement locations, and thus it may be required for a third party to read gradations, or the like. However, according to the length measurement device 1 of the present embodiment, since a user can know the length of a desired location on the display 26 merely by winding the tape portion 10 on the portion, it is possible for the user to ascertain a length independently and simply even in the measurement of any location such as a shoulder length or an arm circumference.

In addition, the electrical impedance between each of the pairs of electrode pads is measured using an alternating-current voltage signal of a predetermined frequency which is generated by the oscillation source 22, and thus is not required to be acquired by bringing the electrode pads 100a, 100b, . . . into direct contact with the measuring object X. Therefore, in the same manner as that of the normal measure, it is possible to perform length measurement by winding the tape portion 10, for example, with clothes on. In addition, thereby, it is also possible to configure the electrode pads 100a, 100b, . . . so as to be covered with the coated portion 12 formed of a resin, a fiber or the like (see FIGS. 2, 3A and 3B), and to prevent the electrode pads 100a, 100b, . . . or the like from rusting or being altered.

As described above, according to the length measurement device of the first embodiment, it is possible to reduce a burden of a user during the measurement of a length.

Modified Example of First Embodiment

The length measurement device 1 according to the first embodiment is not limited to the above-described aspect, and can be modified, for example, as follows.

Figure 8:
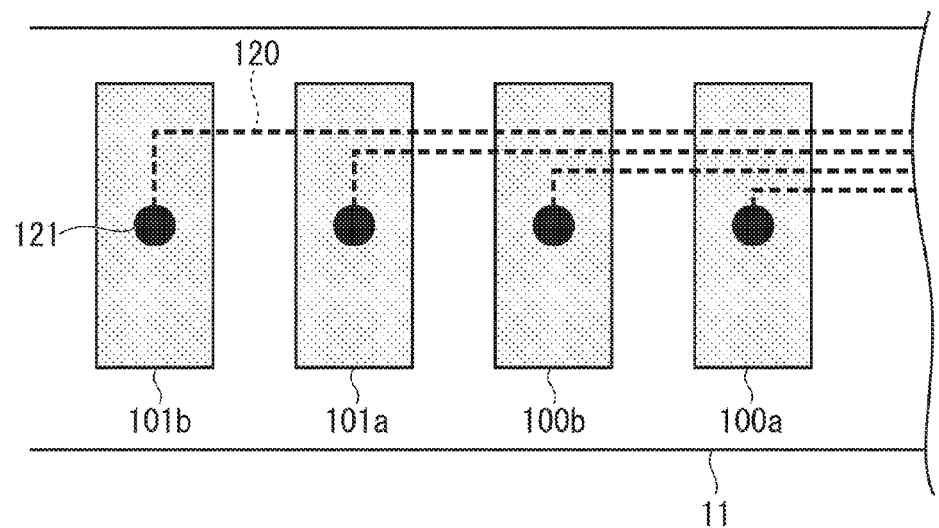
FIG. 8 is a diagram illustrating a configuration of a tape portion of a length measurement device according to a modified example of the first embodiment.

FIG. 8 is a diagram illustrating a configuration of the tape portion of the length measurement device according to a modified example of the first embodiment.

As shown in FIGS. 3A and 3B, a description has been given of a case where the tape portion 10 of the length measurement device 1 according to the first embodiment is constituted by the flexible substrate 11 having a total of three conductor layers of the signal wiring portion 100 and the shield portions 111 and 112 laminated therein. However, the length measurement device 1 according to the modified example of the first embodiment is not limited to such an aspect.

For example, in the length measurement device 1 according to the modified example, as shown in FIG. 8, the routing wirings 120 may be formed in a layer different from a layer having the electrode pads 100a, 100b, . . . formed therein. In this case, contact portions 121 penetrating an interlayer between a layer having the electrode pads 100a, 100b, . . . formed therein and a layer having the routing wirings 120 formed therein are provided, and each tape portion 10 and the routing wirings 120 are connected to each other through these contact portions 121.

In this manner, as shown in FIG. 8, it is possible to array the routing wirings 120 on the back side of the electrode pads 100a, 100b, . . . , and to thereby reduce the size of the entirety of the tape portion 10. Meanwhile, in this case, a conductor layer is further added between the layer having the electrode pads 100a, 100b, . . . formed therein and the layer having the routing wirings 120 formed therein, and thus a shield layer that covers only a conductor layer having the routing wirings 120 formed therein may be further formed.

Figure 9:
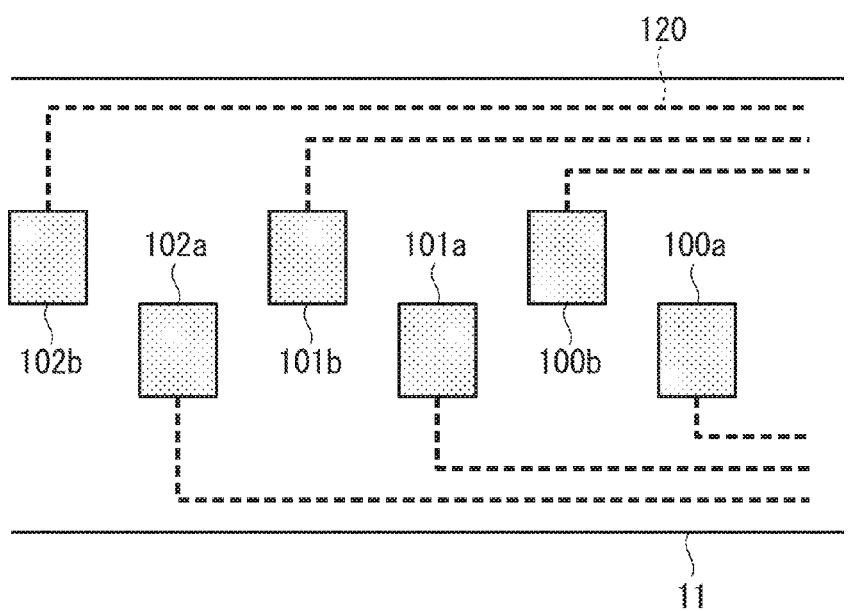
FIG. 9 is a diagram illustrating a configuration of a tape portion of a length measurement device according to another modified example of the first embodiment.

FIG. 9 is a diagram illustrating a configuration of a tape portion of a length measurement device according to another modified example of the first embodiment.

As shown in FIG. 9, in the length measurement device 1 according to another modified example, an aspect may be used in which the electrode pads 100a, 100b, . . . are periodically arrayed in a zigzag on the tape portion 10. In this manner, when the electrical impedance between one pair of electrode pads is acquired, it is possible to reduce the influence of electromagnetic interference between electrode pads adjacent to each other.

For example, in the first embodiment, when the impedance acquisition unit 210 is attempted to acquire the electrical impedance between the electrode pads 101a and 101b in FIG. 3A, a case is assumed in which an electric field generated between the electrode pads 101a and 101b causes an error under the influence of the electrode pad 100b and the electrode pad 102a, adjacent to each other, due to capacitive coupling.

However, according to the length measurement device 1 of the modified example shown in FIG. 9, the electrode pads 100a, 100b, . . . are arrayed in a zigzag. Thereby, for example, when the electrical impedance between the electrode pads 101a and 101b shown in FIG. 9 is acquired, capacitive coupling between the electrode pad 100b and the electrode pad 102a adjacent to each other is reduced, and thus it is possible to keep the influence thereof to a minimum.

In addition, a description has been given of a case where the routing wirings 120 of the length measurement device 1 according to the first embodiment are connected one by one for each of the electrode pads 100a, 100b, . . . and are routed up to the main unit 20. However, the length measurement device 1 according to another modified example is not limited to such an aspect. For example, the tape portion 10 of the length measurement device 1 according to the modified example has a multiplexer included therein, and one routing wiring 120 is shared in a plurality of electrode pads 100a, 100b, . . . by this multiplexer. In this case, the control unit 21 controls this multiplexer, and performs a process of selecting which electrode pad one routing wiring 120 is connected to. With this configuration, one control line of the multiplexer is added, but nine routing wirings can be reduced, for example, when one routing wiring 120 is shared in ten electrode pads.

In this manner, it is possible to reduce the number of routings to be formed within the tape portion 10 (flexible substrate 11), and to reduce the size of the tape portion 10.

In addition, a description has been given of a case where the length measurement device 1 according to the first embodiment acquires electrical impedance in non-contact with the measuring object X, using an alternating-current voltage signal of a predetermined frequency. However, the length measurement device 1 according to another modified example of the first embodiment may read whether the facing surfaces of the electrode pads 100a, 100b, . . . come into direct contact with the measuring object X, to measure the length thereof. In this case, for example, the tape portion 10 is configured such that the coated portion 12 (FIG. 3B) on the "surface side U" is not provided, and that the facing surfaces of the electrode pads 100a, 100b, . . . are arrayed in an exposed state. In addition, similarly to the first embodiment, the control unit 21 reads whether the electrode pads 100a, 100b, . . . come into direct contact with the measuring object X, through the comparison of the electrical impedance between a pair of electrode pads with the predetermined determination threshold.

In this manner, the length measurement device 1 according to the modified example performs length measurement while determining whether the facing surfaces of the electrode pads 100a, 100b, . . . come into direct contact with the measuring object X, and thus it is possible to obtain a higher-accuracy measurement result. In addition, since the surface of the measuring object X comes into direct contact with the facing surfaces of the electrode pads 100a, 100b, . . . , a relatively low frequency can be used in the alternating-current voltage signal which is output by the oscillation source 22. Thus, it is possible to simplify the entire configuration of a circuit.

In addition, a so-called two-electrode method is used in which the impedance acquisition unit 210 of the length measurement device 1 according to the above-described first embodiment selects two out of the electrode pads 100a, 100b, . . . , and performs the application and measurement of an alternating-current voltage signal therebetween, but the length measurement device 1 according to another embodiment is not limited to such an aspect. For example, the impedance acquisition unit 210 of the length measurement device 1 according to the another embodiment may acquire electrical impedance by selecting four out of the electrode pads 100a, 100b, . . . , applying an alternating-current voltage signal between a pair of electrode pads located on both ends, and measuring a voltage and a current which are generated between a pair of electrode pads located inside. In this manner, the impedance acquisition unit 210 can perform high-accuracy electrical impedance measurement having a reduction in error factors due to the electrode pads 100a, 100b, . . . , the routing wirings 120, and the like.

In addition, an aspect has been described in which the length measurement device 1 according to the above-described first embodiment is configured such that the tape portion 10 is constituted by the flexible substrate 11 having the electrode pads 100a, 100b, . . . , the shield portions 111 and 112, and the like patterned and laminated therein, and the coated portion 12 that covers the entirety thereof. However, the aspect in which the flexible substrate 11 is used in the tape portion 10 is merely an example, and the tape portion 10 can also be configured by other methods.

For example, in the length measurement device 1 according to another modified example of the first embodiment, the tape portion 10 may be fabricated in the combination of a conductive fiber having conductive properties and a non-conductive fiber (fiber having normal insulating properties). Specifically, instead of the flexible substrate 11, a fiber (electrode fiber) having the conductive fiber woven in the same pattern as that of the layouts (FIG. 3A) of the electrode pads 100a, 100b, . . . and the routing wirings 120 may be adopted in the tape portion 10. In addition, in this case, the tape portion may be configured to interpose the electrode fiber with a fiber (shield fiber) having a conductive fiber woven in the same pattern (FIG. 3A) as that of the shield portions 111 and 112. In this manner, the same configuration as that of the flexible substrate 11 in the first embodiment can be fabricated by only the conductive fiber and normal fiber. Thereby, it is possible to more inexpensively fabricate the tape portion 10, and to achieve a reduction in the manufacturing cost of the length measurement device 1.

The length measurement device 1 according to the above-described embodiment may have a storage unit included therein, and have a function of being capable of storing a plurality of pieces of length information which are continuously acquired. Specifically, the length calculation unit 211 stores and accumulates the pieces of length information, sequentially calculated, in the storage unit which is separately provided. In this case, the length measurement device 1 may have a function of being capable of arbitrarily displaying the plurality of pieces of length information, stored and accumulated in the storage unit, on the display 26 in accordance with a user's operation.

In this manner, when a user continuously measures, for example, the width, length, depth and the like of a measuring object, the user does not need to take a memo or the like for each of the pieces of length information continuously measured, and thus it is possible to make measurement work efficient.

In addition, the length measurement device 1 may have a predetermined communication unit included therein, and have a function of transmitting length information calculated by the length calculation unit 211 or length information accumulated in the storage unit to an outside server through this communication unit. In this case, the length measurement device 1 may have a function of continuously recording a plurality of pieces of length information to an outside server (also inclusive of a smartphone or the like), and sequentially reading these pieces of length information, as necessary.

Second Embodiment

Next, a length measurement device according to a second embodiment will be described with reference to the accompanying drawings.

Since functional components of a length measurement device 1 according to the second embodiment are the same as the functional components of the length measurement device 1 according to the first embodiment, the functional components thereof are not shown in the drawings. Respective function units are denoted by the same reference numerals and signs, and thus the description thereof will not be given.

The length measurement device 1 according to the second embodiment is different from that of the first embodiment, in that the process details of the control unit 21 (impedance acquisition unit 210 and length calculation unit 211) are different from each other. Hereinafter, the functions of the impedance acquisition unit 210 and the length calculation unit 211 according to the second embodiment will be described with reference to FIG. 4.

The impedance acquisition unit 210 according to the second embodiment first selects a plurality of pairs of electrode pads 100a, 100b, . . . which are arrayed at a first separation distance, and performs a first acquiring step of acquiring electrical impedance therebetween for each of the plurality of pairs of electrode pads. Next, the impedance acquisition unit 210 selects a plurality of pairs of electrode pads which are arrayed at a second separation distance larger than the first separation distance, and performs a second acquiring step of acquiring electrical impedance therebetween for each of the plurality of pairs of electrode pads.

Here, for example, a description will be given in which the first separation distance is set to a distance between electrode pads adjacent to each other, and the second separation distance is set to a separation distance equivalent to three electrode pads.

That is, in this case, in the first acquiring step, the impedance acquisition unit 210 acquires electrical impedance for each of the pairs of electrode pads (for example, a pair of electrode pads 100a and 100b, a pair of electrode pads 101a and 100b, a pair of electrode pads 101a and 101b, . . . ) adjacent to each other. A process of acquiring electrical impedance according to this first acquiring step has the same process details as those of the impedance acquisition unit 210 according to the first embodiment.

The impedance acquisition unit 210 according to the second embodiment further performs the second acquiring step after the first acquiring step. Specifically, in the second acquiring step, the impedance acquisition unit 210 acquires electrical impedance therebetween for each of the pairs of electrode pads spaced at a separation distance equivalent to three electrode pads. For example, in the second acquiring step, the impedance acquisition unit 210 selects the electrode pad 100a and the electrode pad 101b which is arrayed at a distance equivalent to three electrode pads from this electrode pad 100a, and acquires electrical impedance between this pair of electrode pads.

In addition, the length calculation unit 211 according to the second embodiment calculates a length $\Delta A$ with reference to both the electrical impedance acquired in the first acquiring step and the electrical impedance acquired in the second acquiring step. The specific processing details will be described with reference to flow diagrams (FIGS. 12 and 13) described later.

Figure 10A:
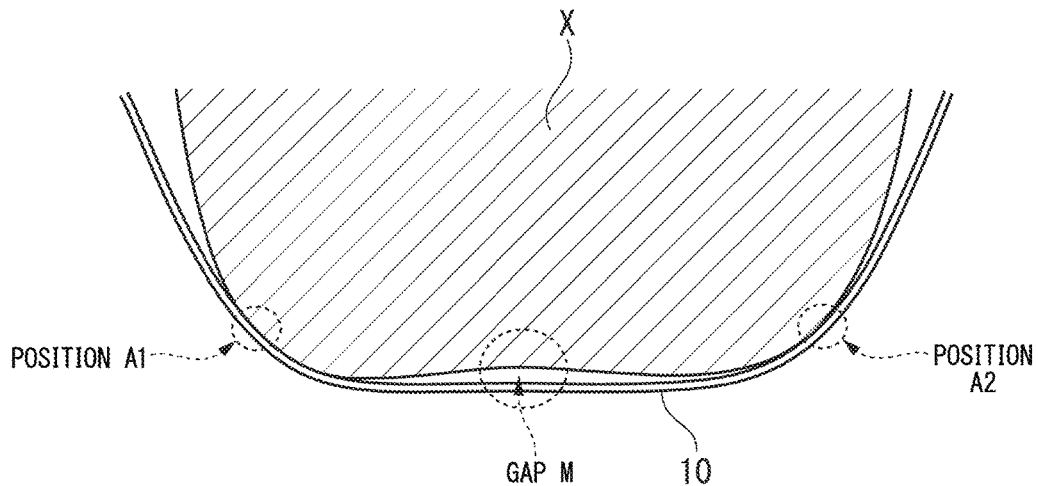
FIG. 10A is a first diagram illustrating an action of a length measurement device according to a second embodiment.
Figure 10B:
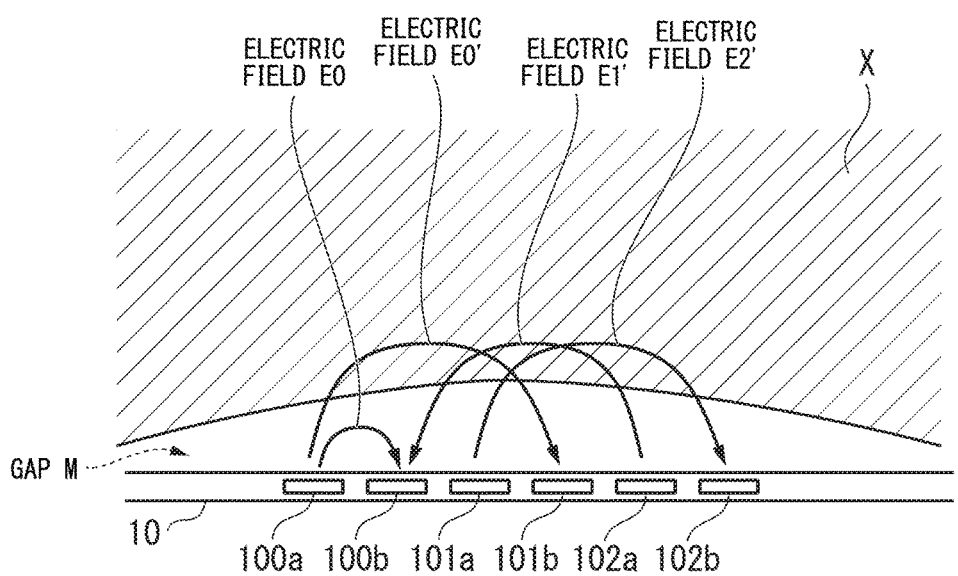
FIG. 10B is a second diagram illustrating an action of the length measurement device according to the second embodiment.

FIGS. 10A and 10B are a first diagram and a second diagram, respectively, illustrating an action of the length measurement device according to the second embodiment.

FIG. 10A shows a state where the tape portion 10 is arrayed so as to be wound around a portion of the periphery of the measuring object X.

As shown in FIG. 10A, the tape portion 10 is arrayed from the position A1 to the position A2 so as to be wound along the periphery of the measuring object X which is a living body. The tape portion 10 is in proximity of the measuring object X in the peripheries of the position A1 and the position A2, but has a gap M in a portion of an area between the position A1 and the position A2, and has an area which is slightly separated from the measuring object X. In this manner, in a case where the length measurement device 1 is used in the length measurement of a living body, a situation is assumed in which a gap occurs between a portion of the tape portion 10 and the measuring object X, due to the influence of irregularities of a body, wrinkles of clothes, or the like, depending on the location of the measuring object X (living body) to be wound.

FIG. 10B is a diagram particularly illustrating a portion where the gap M of the tape portion 10 in a state shown in FIG. 10A exists.

For example, in the vicinity of the gap M, it is assumed that the electrode pads 100a, 100b, 101a, 101b, 102a, and 102b are arrayed as shown in FIG. 10B. In this case, based on the first acquiring step, the impedance acquisition unit 210 sequentially acquires for example, electrical impedances between the electrode pads 100a and 100b, between the electrode pads 101a and 100b, between the electrode pads 101a and 101b, . . . , and electrical impedances between pairs of electrode pads adjacent to each other while changing the pairs of electrode pads in order.

Here, in the area of the gap M, attention is focused on an electric field E0 which is generated between the electrode pads 100a and 100b adjacent to each other. In this case, since the generation area of an electric field E0 is restricted to be narrow in accordance with the separation distance between the electrode pads 100a and 100b, the generation area of the electric field E0 does not include the measuring object X existing with the gap M interposed. Therefore, the electrical impedance between the electrode pads 100a and 100b is not influenced by the presence or absence of the measuring object X, and the same high value as that of electrical impedance acquired in a range not being in proximity to the measuring object X is acquired. The same is true of the electrical impedances acquired between the electrode pads 101a and 100b and between the electrode pads 101a and 101b.

That is, in a case where the gap M occurs between the tape portion 10 and the measuring object X, it is not possible to sense the measuring object X existing with the gap M interposed, through the electric field (electric field E0) generated between electrode pads adjacent to each other.

Next, the second acquiring step which is performed by the impedance acquisition unit 210 according to the present embodiment will be described with reference to FIG. 10B.

In the second acquiring step according to the above-described example, the impedance acquisition unit 210 acquires electrical impedance between a pair of electrode pads spaced at a separation distance equivalent to three electrode pads. Specifically, as shown in FIG. 10B, the electrical impedance between the electrode pads 100a and 101b, between the electrode pads 100b and 102a, between the electrode pads 101a and 102b, . . . are sequentially acquired.

In this case, since the interval between a pair of electrode pads is greater than that when acquired in the first acquiring step, the generation areas of electric fields (electric fields E0', E1', and E2' in FIG. 10B) generated therebetween are also expanded accordingly. Therefore, as shown in FIG. 10B, the electric fields E0', E1', and E2' pass through the area of the measuring object X existing with the gap M interposed, and thus the electrical impedance between each of the pairs of electrode pads decreases under the influence of the measuring object X.

In this manner, in the second acquiring step, it is possible to detect the existence of the measuring object X even in the area where the gap M exists.

Figure 11:
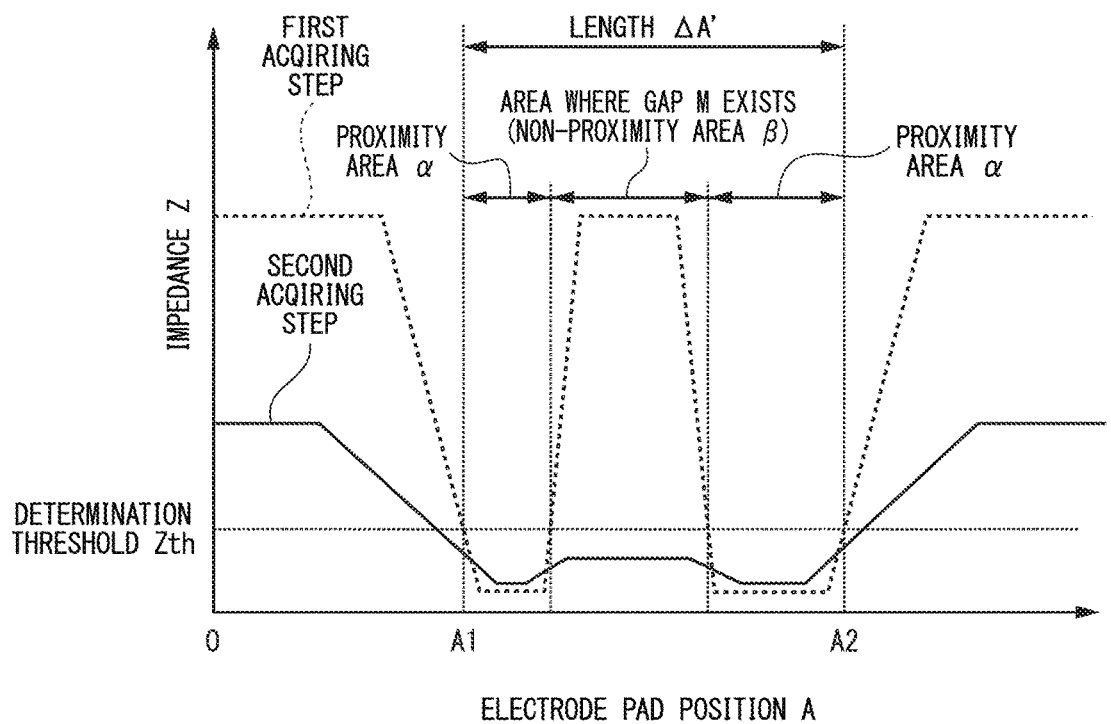
FIG. 11 is a third diagram illustrating an action of the length measurement device according to the second embodiment.

FIG. 11 is a third diagram illustrating an action of the length measurement device according to the second embodiment.

Similarly to FIG. 6, in a graph shown in FIG. 11, the horizontal axis represents the position A of the tape portion 10, and the vertical axis represents the electrical impedance Z between a pair of electrodes which are arrayed at the position A. In addition, the electrical impedance acquired in the first acquiring step is shown by a broken line, and the electrical impedance acquired in the second acquiring step is shown by a solid line.

As described in FIG. 10B, the electrical impedance Z which is acquired in the first acquiring step by the impedance acquisition unit 210 is not influenced by the measuring object X in the area where the gap M exists, and thus the electrical impedance is detected to be high in the area where the gap M exists, as shown by the broken line of FIG. 11. Therefore, when the length calculation unit 211 makes a determination based on the determination threshold Zth, a plurality of proximity areas α which are areas being set to be below the determination threshold Zth exist with a non-proximity area β which is an area exceeding the determination threshold Zth interposed therebetween, and thus a length ΔA' which a user attempts to know originally may not be able to be correctly calculated.

On the other hand, since the electrical impedance Z which is acquired in the second acquiring step by the impedance acquisition unit 210 is influenced by the measuring object X even in the area where the gap M exists, the electrical impedance is detected to be low even in the area where the gap M exists, as shown by the solid line of FIG. 11. Therefore, the length calculation unit 211 can determine that the measuring object X is in continuity between the position A1 to the position A2, on the basis of the determination based on the determination threshold Zth, and can correctly calculate the length ΔA' thereof.

Figure 12:
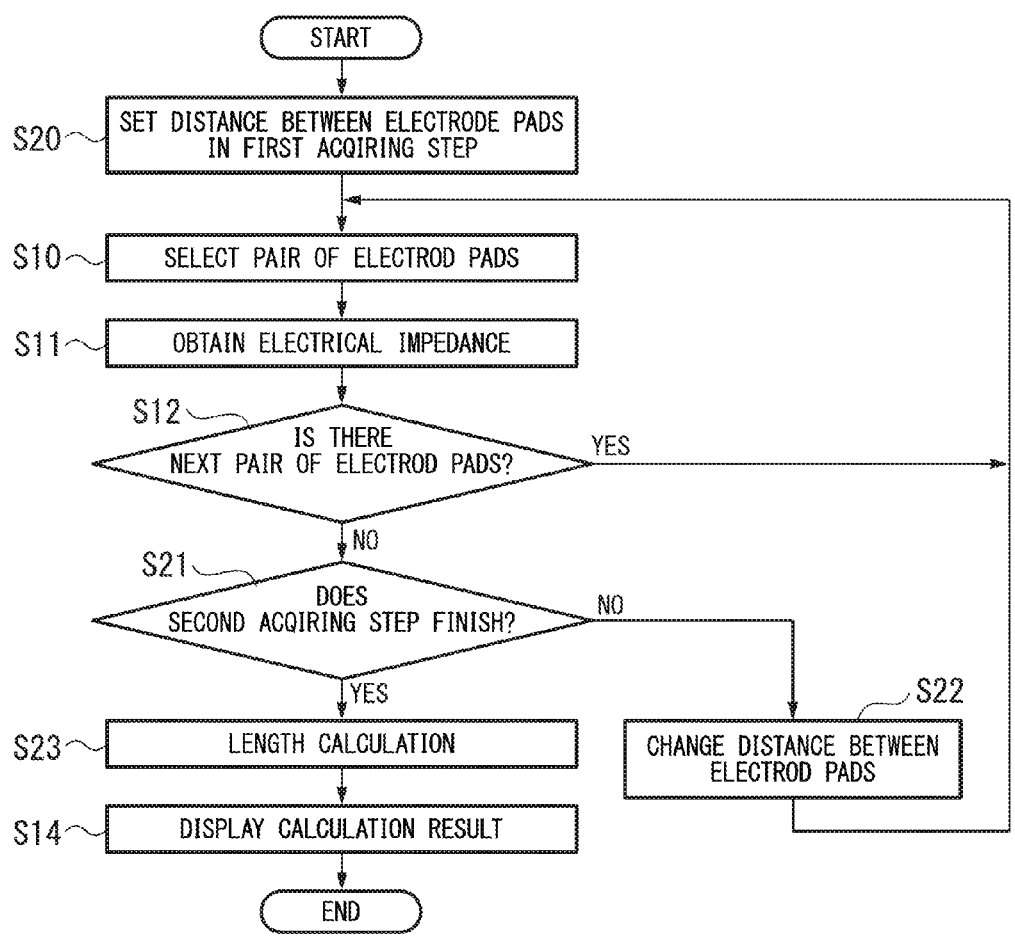
FIG. 12 is a first diagram illustrating a process flow of a control unit of the length measurement device according to the second embodiment.

FIG. 12 is a first diagram illustrating a process flow of the control unit of the length measurement device according to the second embodiment.

The process flow of the control unit 21 having the functions described above will be described in order with reference to FIG. 12. Meanwhile, the same processing details as those in the first embodiment are denoted by the same reference numerals and signs, and thus the description thereof will not be given.

The process flow of the control unit 21 shown in FIG. 12 starts immediately after an operation in a state where a user can use the length measurement device 1 is performed (for example, immediately after a main power is on).

First, the impedance acquisition unit 210 of the control unit 21 starts the first acquiring step. In this case, the impedance acquisition unit 210 sets a distance (separation distance d="1") between electrode pads adjacent to each other, as a distance between the electrode pads selected in the first acquiring step (step S20).

Next, in steps S10 to S12, the impedance acquisition unit 210 sequentially acquires electrical impedances between each of the pairs of electrode pads while selecting the electrode pads 100a and 100b, 101a and 100b, . . . adjacent to each other. When the electrical impedances of all the pairs of electrode pads are acquired (step S12: NO), the first acquiring step is finished, and the process proceeds to step S21.

Next, the impedance acquisition unit 210 determines whether the second acquiring step finishes (step S21). Here, in a case where only the first acquiring step finishes (step S21: NO), the process proceeds to step S22. On the other hand, in a case where the second acquiring step finishes (step S21: YES), the process proceeds to step S13.

In a case where the first acquiring step finishes, the impedance acquisition unit 210 starts the second acquiring step. In this case, the impedance acquisition unit 210 changes a distance between electrode pads to be selected, to a separation distance larger than the separation distance in the first acquiring step, for example, a separation distance equivalent to three electrode pads (separation distance d="3") (step S22).

Next, in steps S10 to S12, the impedance acquisition unit 210 sequentially acquires electrical impedances between each of the pairs of electrode pads again while selecting the electrode pads 100a and 101b, 102a and 100b, . . . spaced at a separation distance equivalent to three electrode pads. When the electrical impedances between all the pairs of electrode pads are acquired (step S12: NO), the second acquiring step is finished, and the process proceeds to step S23 through step S21.

In a case where the electrical impedances are acquired through the first acquiring step and the second acquiring step, the length calculation unit 211 according to the present embodiment refers to these electrical impedances to perform a process of calculating the length ΔA of the measuring object X (step S23). The specific details of the calculation process in step S23 will be described later.

The length calculation unit 211 outputs length information indicating the calculated length ΔA to the display 26, displays a calculation result (measurement result of the length) (step S14), and finishes the measurement process. Thereby, a user can ascertain the length of the measuring object X (area between the positions A1 and A2).

Meanwhile, similarly to the first embodiment, the control unit 21 of the length measurement device 1 according to the present embodiment may stand by for a certain period of time after the finish of step S14, and then returns to step S10 to periodically repeat a series of measurement processes of steps S10 to S14. In addition, the control unit 21 may perform a series of measurement processes of steps S10 to S14, based on the detection of pressing down of a "measurement start button" which is separately provided in the main unit 20.

Figure 13:
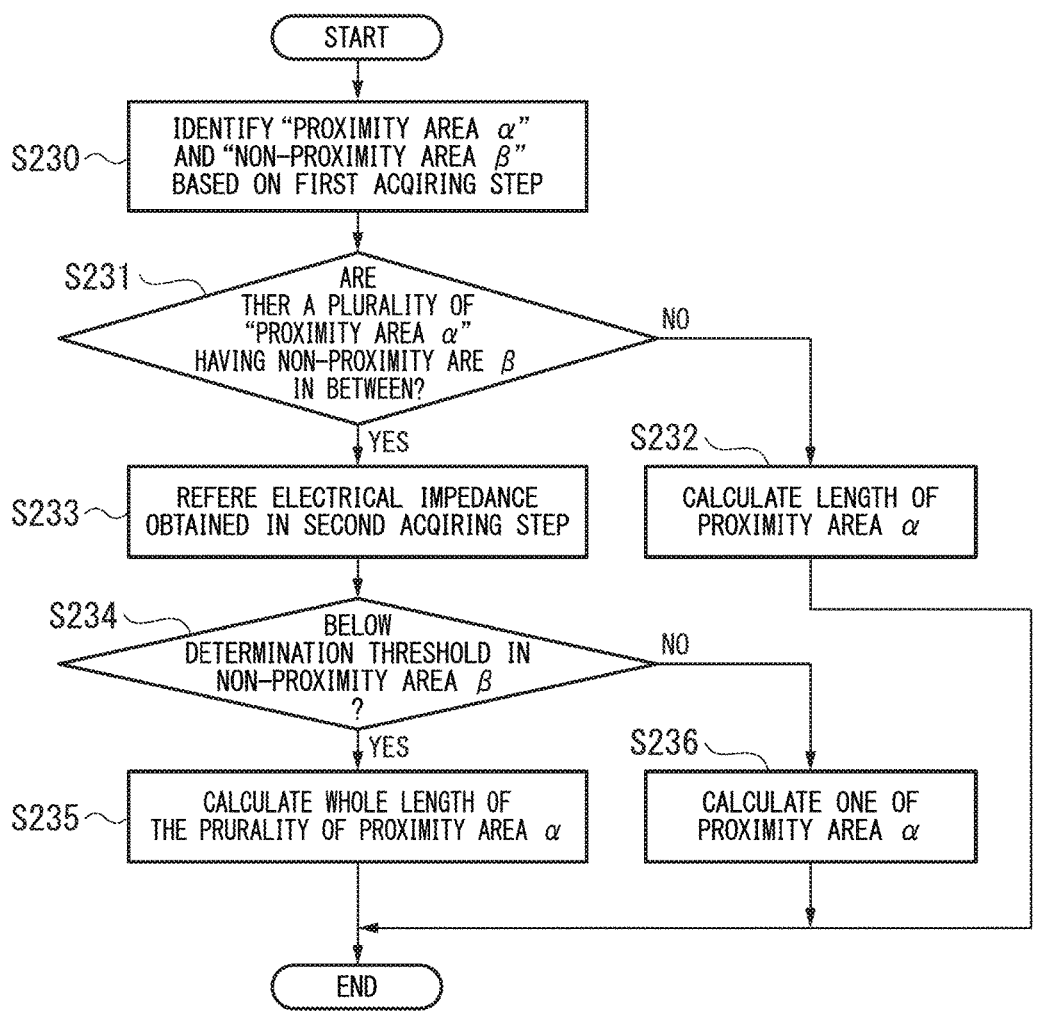
FIG. 13 is a second diagram illustrating a process flow of the control unit of the length measurement device according to the second embodiment.

FIG. 13 is a second diagram illustrating a process flow of the control unit of the length measurement device according to the second embodiment.

Next, the process of calculating the length ΔA which is executed by the length calculation unit 211 (FIG. 12, step S23) will be described with reference to FIG. 13.

Similarly to the first embodiment, the length calculation unit 211 according to the present embodiment first identifies the "proximity area α" which is an area where the electrical impedance Z acquired in the first acquiring step is set to be below the determination threshold Zth and the "non-proximity area β" which is an area where the electrical impedance exceeds the determination threshold Zth (step S230).

Next, when the identification of the proximity area α and the non-proximity area β is completed, the length calculation unit 211 determines whether a plurality of proximity areas α exist with the non-proximity area β interposed therebetween (step S231). Specifically, the length calculation unit 211 refers to the electrical impedance values Z acquired for each of the pairs of electrode pads in order, to identify an interval where pairs of electrode pads in which the impedance value is set to be below the determination threshold Zth continuously exist, as one "proximity area α". In a case where the area of the "non-proximity area β" after that continues, and then a pair of electrode pads in which the electrical impedance value Z is set to be below the determination threshold Zth appear again, this is identified as a second "proximity area α".

For example, in a case of the state as shown in FIG. 11, a plurality of (two) proximity areas α exist due to the existence of the gap M with the non-proximity area β interposed therebetween. In this case, the length calculation unit 211 determines "YES" in step S231.

In a case where the non-proximity area β does not exist and only one proximity area α exists (step S231: NO), the length calculation unit 211 performs the same process as that in the first embodiment. That is, the length calculation unit 211 calculates the length ΔA (=A1−A2) of the single proximity area α (step S232).

On the other hand, in a case where a plurality of proximity areas α exist with the non-proximity area β interposed therebetween (step S231: YES), the length calculation unit 211 refers to the electrical impedance acquired in the second acquiring step (step S233).

Here, the length calculation unit 211 determines whether the electrical impedance Z acquired in the second acquiring step is set to be below the determination threshold Zth, in a pair of electrode pads corresponding to the non-proximity area β identified in the first acquiring step (step S234).

In a case where the electrical impedance Z acquired in the second acquiring step is set to be below the determination threshold Zth, in the pair of electrode pads corresponding to the non-proximity area β identified in the first acquiring step (step S234: YES), the length calculation unit 211 regards the measuring object X as existing in the non-proximity area β with a slight gap (gap M) interposed therebetween, and calculates the length ΔA' (FIG. 11) of the entire area where the plurality of proximity areas α exist with the non-proximity area β interposed therebetween (step S235).

On the other hand, in a case where the electrical impedance Z acquired in the second acquiring step exceeds the determination threshold Zth again in the non-proximity area β (step S234: NO), the length calculation unit 211 regards the measuring object X indicating the plurality of proximity areas α as being separated, and calculates any length Δα (of the proximity area α, for example, having a largest length) (step S236).

Even in a case of the situation where the gap M as shown in, for example, FIGS. 10A and 10B exists, through such a process, the length calculation unit 211 regards the measuring object X existing in the area (non-proximity area β), and can calculate a length (length ΔA' of the range between the position A1 and position A2) which a user attempts to know in reality.

As described above, according to the length measurement device 1 of the second embodiment, even in a state where a slight gap occurs between the tape portion 10 and the measuring object X, it is possible to accurately measure a user's desired length without a fluctuation in a measurement result depending on the presence or absence of the gap.

Meanwhile, a description has been given of a case where the length measurement device according to the above-described second embodiment performs the first acquiring step of acquiring electrical impedance between electrode pads adjacent to each other and the second acquiring step of acquiring electrical impedance between electrode pads spaced at a larger separation distance, but the length measurement device according to the modified example of the present embodiment is not limited to such a method. For example, the length measurement device according to the modified example may perform a third acquiring step and a fourth acquiring step of acquiring electrical impedance between electrode pads spaced at a separation distance larger than the distance between electrode pads in the second acquiring step.

Third Embodiment

Next, a length measurement device according to a third embodiment will be described with reference to the accompanying drawings.

Figure 14:
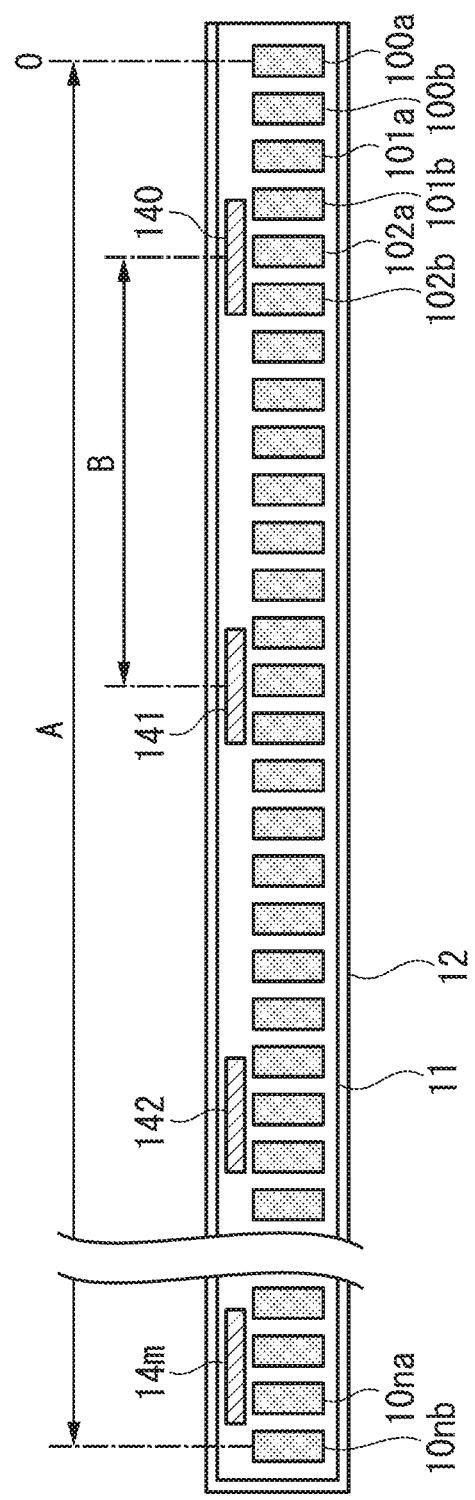
FIG. 14 is a diagram illustrating a configuration of a tape portion of a length measurement device according to a third embodiment.

FIG. 14 is a diagram illustrating a configuration of the tape portion of the length measurement device according to the third embodiment. Meanwhile, the same components as those in the first embodiment are denoted by the same reference numerals and signs, and thus the description thereof will not be given.

As shown in FIG. 14, the tape portion 10 of the length measurement device 1 according to the third embodiment is configured such that a plurality of strain gauges 140, 141, . . . 14m (m is an integer of 1 or greater) which are an aspect of a curvature sensor are periodically arrayed at a constant interval B along a longitudinal direction.

Each of the strain gauges 140, 141, . . . is a sensor that outputs a detection signal according to the degree of strain (bending) which is given to itself.

In the present embodiment, the strain gauges 140, 141, . . . are formed on the same surface (see the signal wiring portion 100 in FIG. 3B) as the electrode pads 100a, 100b, . . . and the routing wirings 120 are formed. Therefore, the strain gauges 140, 141, . . . are arrayed in an area in the in-plane of the tape portion 12 where the electrode pads 100a, 100b, . . . are not arrayed.

Figure 15:
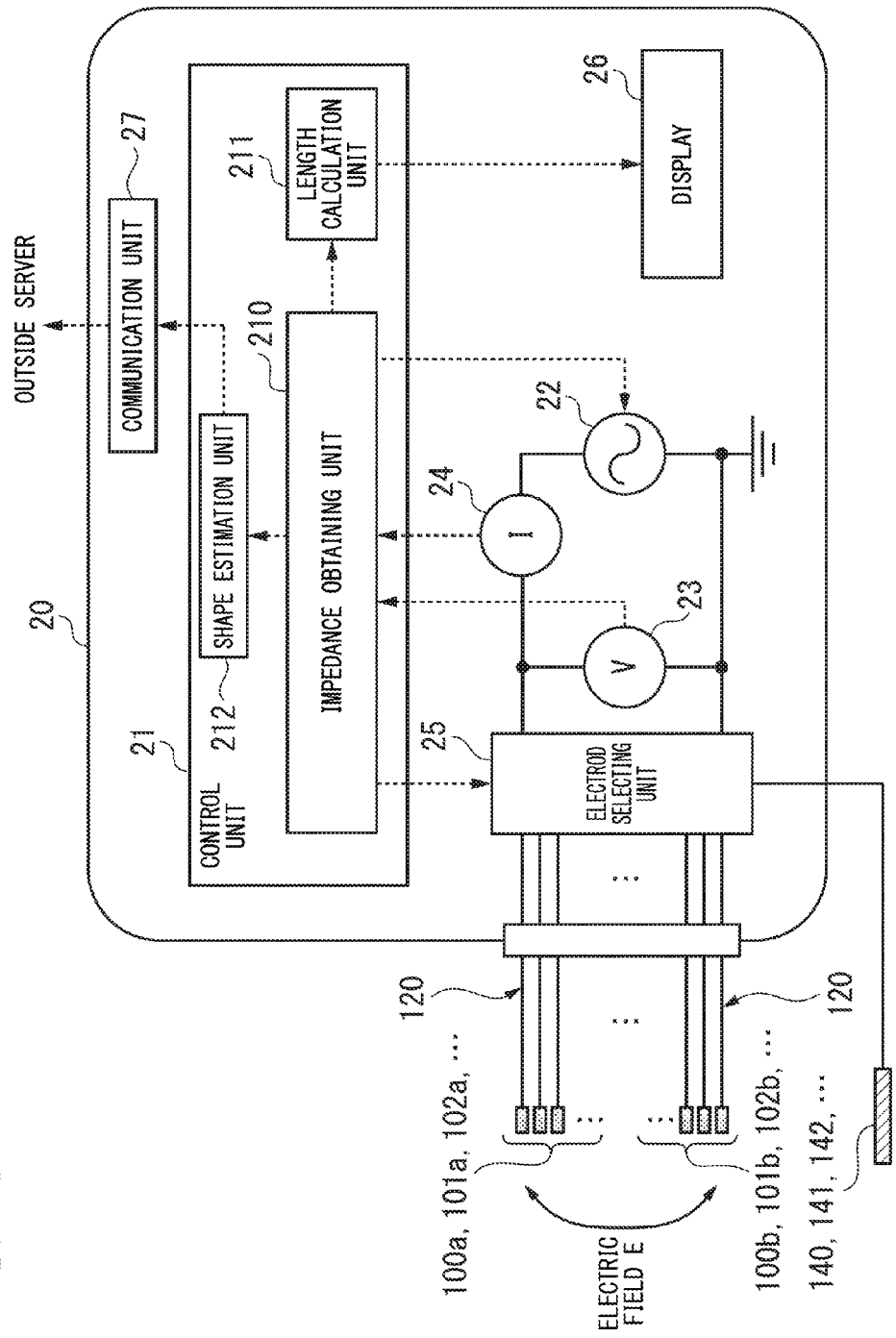
FIG. 15 is a diagram illustrating functional components of a main unit of the length measurement device according to the third embodiment.

FIG. 15 is a diagram illustrating functional components of the main unit of the length measurement device according to the third embodiment.

The same functional components as those in the first embodiment are denoted by the same reference numerals and signs, and thus the description thereof will not be given.

As shown in FIG. 15, the main unit 20 of the length measurement device 1 according to the third embodiment includes a shape estimation unit 212 in the control unit 21.

The shape estimation unit 212 estimates the shape of the portion (FIG. 5A) around which the tape portion 10 is wound in the measuring object X, based on a detection signal indicating each strain state acquired from the strain gauges 140, 141, . . . .

Specifically, the impedance acquisition unit 210 first supplies a predetermined input signal to each of the strain gauges 140, 141, . . . through the electrode selecting unit 25. Next, the impedance acquisition unit 210 acquires a response signal to the input signal of each of the strain gauges 140, 141, . . . , that is, a detection signal according to the radius of curvature. The impedance acquisition unit 210 outputs the acquired detection signal to the shape estimation unit 212.

The shape estimation unit 212 can previously ascertain, for example, information of the interval B arrayed on the tape portion 10, and can estimate the shape of the tape portion 10 wound around the measuring object X by combining this information with radius of curvatures r0, r1, . . . calculated from the detection signal in each of the selected strain gauges 140, 141, . . . .

In addition, the shape estimation unit 212 may refer to the "proximity area α" which is identified based on the electrical impedance acquired from the electrode pads 100a, 100b, . . . , and estimate the shape of the portion related to the "proximity area α" of the tape portion 10, using the detection signal supplied from only the strain gauges 140, 141, . . . belonging to the "proximity area α".

In this manner, a user can ascertain not only the length of the portion around the tape portion 10 is wound, but also the shape of the portion. Therefore, pieces of shape information corresponding to items such as, for example, the bust, waist, hip are acquired and combined, and thus it is possible to acquire three-dimensional shape information indicating the three-dimensional shape of a body type in a simple manner.

In addition, the length measurement device 1 may be able to transmit the pieces of shape information acquired by the shape estimation unit 212 to an outside server through a communication unit 27 (FIG. 15). In this manner, the pieces of shape information of a personal body type acquired using the length measurement device 1 can be accumulated in an outside server and be appropriately used. For example, a user can quantitatively evaluate the effect of a diet or the like, based on pieces of shape information relevant to his or her body which are periodically acquired.

Meanwhile, in the present embodiment, a description has been given of a case where the strain gauges 140, 141, . . . are formed on the same surface (signal wiring portion 100) as the electrode pads 100a, 100b, . . . are formed, but other embodiments are not limited to such an aspect. For example, the strain gauges 140, 141, . . . may be formed in a layer different from that in which the electrode pads 100a, 100b, . . . are formed in the flexible substrate 11.

In this case, the layer (signal wiring portion 100) having the electrode pads 100a, 100b, . . . formed therein and the layer having the strain gauges 140, 141, . . . formed therein are electrically isolated from each other with one or more insulating layers (and, shield layers in some cases) interposed therebetween.

In addition, in this case, an aspect may be used in which each of the strain gauges 140, 141, . . . is formed so as to overlap each of the electrode pads 100a, 100b, . . . formed in another layer (signal wiring portion 100) and be incident with each other in an interlayer direction, and is thereby formed integrally with the electrode pads 100a, 100b, . . . in appearance. In this manner, it is possible to reduce the area (length in a width direction) of the tape portion 12.

Meanwhile, all the functions of the length measurement devices 1 according to the respective embodiments described above have been described by taking an example in which the perimeter of a "living body" is measured, but the measuring object of the length measurement device 1 according to each of the embodiments is not limited to a "living body", and the length measurement devices can also measure, for example, the dimensions or perimeters of industrial products. In this case, the length measurement device 1 may have a function of changing the determination threshold Zth in accordance with the type of a measuring object (living body, metal, non-metal, or the like). Specifically, an aspect may be used in which the control unit 21 includes a type selecting unit that selects the type of a measuring object by receiving a user's operation. In this case, the type selecting unit changes the value of the determination threshold Zth in accordance with the selected type of a measuring object.

In addition, a description has been given of a case where, when the electrical impedance Z is set to be below the determination threshold Zth, the length calculation unit 211 according to the present embodiment regards an area where a pair of electrode pads having the electrical impedance Z, set to be the below the determination threshold Zth, acquired therein exist, as the "proximity area α", and calculates the length A of this proximity area α. However, other embodiments are not limited to such an aspect. For example, an aspect may be used in which, in a case where the electrical impedance Z is set to be above the determination threshold Zth, the length of an area in which the electrical impedance Z above the determination threshold Zth is acquired is calculated.

Meanwhile, a description has been given of a case where the length measurement device 1 according to the third embodiment accurately estimates the shape of the profile of the measuring object X, based on curvature data acquired from the "strain gauges" (strain gauges 140, 141, . . . ) which are periodically arrayed on the tape portion 10, but the "strain gauge" is nothing more than an aspect of a "curvature sensor" for acquiring curvature data at a position where each of the strain gauges is arrayed. The length measurement device 1 according to the third embodiment not necessarily uses the strain gauge in order to acquire curvature data, and may use a curvature sensor constituted by other aspects capable of acquiring curvature data. An aspect of the curvature sensor includes, for example, a curvature sensor or the like having conductive ink applied thereto. The curvature sensor using this conductive ink is fabricated using a variation in the electrical resistance of the conductive ink applied (printed) onto the surface of a freely-curved substrate by the conductive ink being extended or compressed in association with the curvature of the substrate.

Further, in another embodiment, the curvature sensor may be configured such that two strain gauges (which are the same as the above-described strain gauges 140, 141, . . . ) are formed as a pair. Specifically, the curvature sensor according to the another embodiment is configured such that two strain gauges and resistive elements having a well-known resistance value are electrically connected to each other so as to form a bridge circuit. In this manner, during the generation of a change in temperature or tensile and compressive stress, these error factors influence two strain gauges, and a change in the same characteristics and a change in resistance values in association therewith are caused on the both. Thereby, the detection signal (potential difference) itself does not change, and thus it is possible to reduce error causes acting on the distortion gauge.

In addition, in this case, the two strain gauges may be disposed so as to be lined up in the same layer in the flexible substrate 11, and may be disposed so as to overlap two layers with an insulating layer interposed therebetween.

In addition, an aspect may be used in which a curvature sensor according to still another embodiment is configured such that three or more (for example, four) strain gauges are electrically connected to each other so as to form a bridge circuit.

Fourth Embodiment

Next, a length measurement device according to a fourth embodiment will be described with reference to the accompanying drawings.

Figure 16:
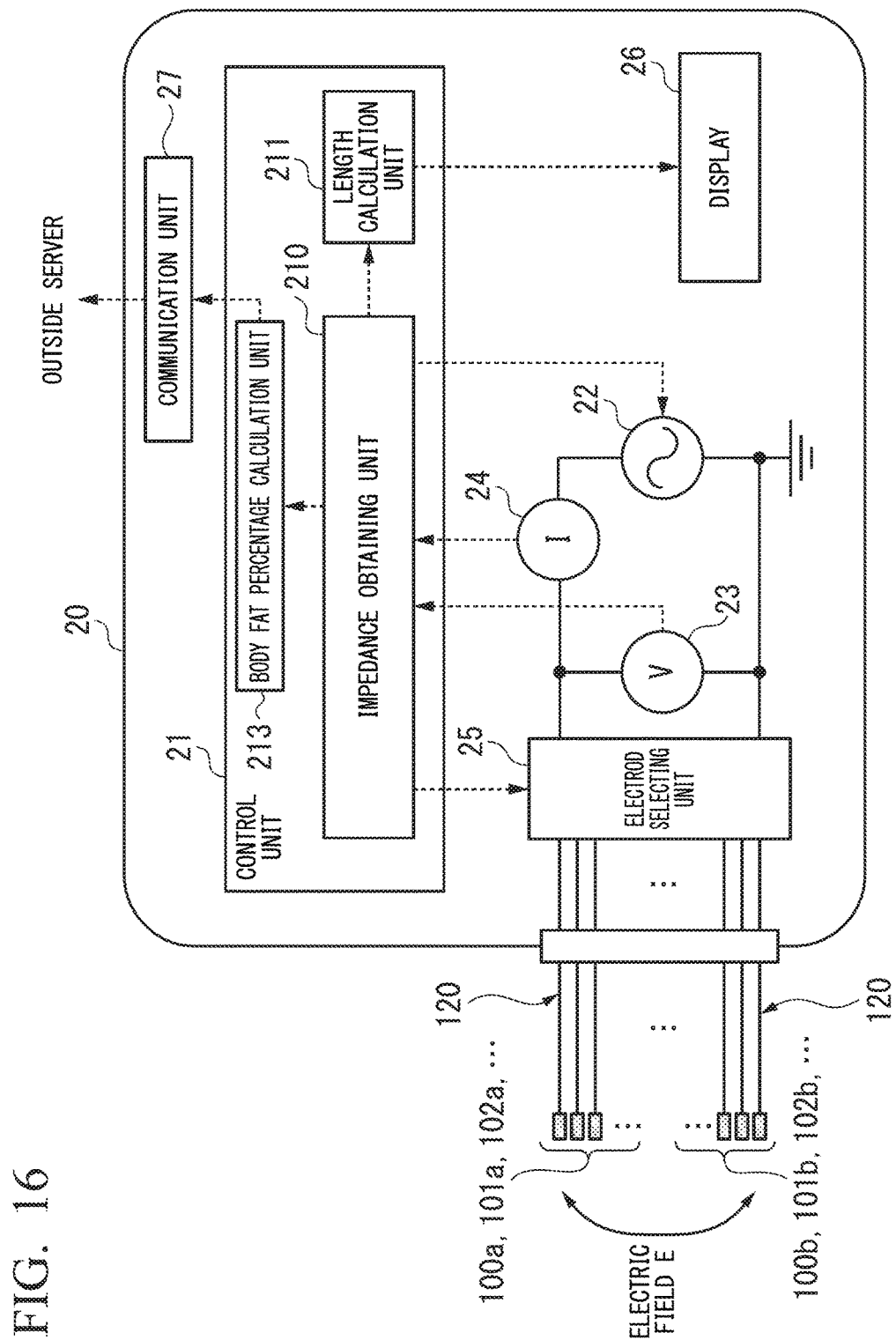
FIG. 16 is a diagram illustrating functional components of a main unit of a length measurement device according to a fourth embodiment.

FIG. 16 is a diagram illustrating functional components of the main unit of the length measurement device according to the fourth embodiment.

The same functional components as those in the first embodiment are denoted by the same reference numerals and signs, and thus the description thereof will not be given. In addition, the configuration of the tape portion 10 of the length measurement device 1 according to the fourth embodiment is the same as that in the first embodiment, and thus is not shown in the drawing.

As shown in FIG. 16, the control unit 21 of the length measurement device 1 according to the present embodiment includes a body fat percentage calculation unit 213.

The body fat percentage calculation unit 213 calculates the body fat percentage of a living body around which the tape portion 10 is wound (accurately, the local fat content in a local portion of a living body around the tape 10 is wound), based on the electrical impedance acquired by the impedance acquisition unit 210. Specifically, the body fat percentage calculation unit 213 analyzes electrical impedance in the identified proximity area α, and calculates the content of body fat in the portion. Meanwhile, as a method of calculating the content of body fat from electrical impedance, a method which is widely and generally known can be used.

Thereby, since the length measurement device 1 according to the present embodiment can calculate the content of local fat in the portion around which the tape portion 10 is wound, a user can ascertain the content of body fat in the local area (such as, for example, upper arms) of his or her body by using the length measurement device 1.

In this case, the impedance measurement unit 210 may have a function of performing a connection through the electrode selecting unit 25 so as to make connection between the electrode pads 100a, 100b, . . . and the oscillation source 22 suitable for body fat percentage measurement. Specifically, for example, the impedance measurement unit 210 may measure impedance for body fat percentage measurement, using electrode pads such as the electrode pads 100a, 100b, 101a, 101b, 102a, and 102b which are continuously arrayed in a predetermined area as "anode electrodes", and using electrode pads such as 107a, 107b, 108a, 108b, 109a, and 109b which are continuously arrayed in another area as "cathode electrodes".

Further, in identifying the areas of the "anode electrode" and the "cathode electrode" for body fat percentage measurement, the impedance measurement unit 210 may identify the areas while referring to the electrical impedance (see FIG. 6) for length measurement which has been performed in advance.

Meanwhile, in calculating the body fat percentage, it is preferable to use the electrical impedance acquired by bringing the electrode pads 100a, 100b, . . . into direct contact with a living body (body), from a point of view of measurement accuracy. However, the length measurement device 1 according to the present embodiment is not limited to such an aspect, and the body fat percentage calculation unit 213 may calculate the body fat percentage based on electrical impedance acquired in non-contact with a living body.

In addition, the length measurement device 1 may transmit the body fat percentage acquired by the body fat percentage calculation unit 213 to an outside server through the communication unit 27 (FIG. 16).

In the aforementioned description, the length measurement device 1 according to each of the embodiments may include a computer system therein. The procedure of each process of the length measurement device 1 described above may be stored in a computer readable recording medium in the form of a program, and each of the above processes may be performed by a computer reading out and executing such a program. The term "computer readable recording medium" as used herein refers to a magnetic disc, a magneto-optic disc, a compact disk read only memory (CD-ROM), a semiconductor memory, or the like. In addition, such a computer program may be delivered to a computer through a communication, and the computer having received this delivery may execute the program.

As stated above, while certain embodiments have been described, these embodiments have been presented by way of example only, and are not intended to limit the scope of the invention. Indeed, these embodiments described herein may be embodied in a variety of other forms; furthermore, various omissions, substitutions and changes in the form of the embodiments described herein may be made without departing from the scope of the inventions. The appended claims and their equivalents are intended to cover such forms or modifications as would fall within the scope of the invention.

Figure 17:
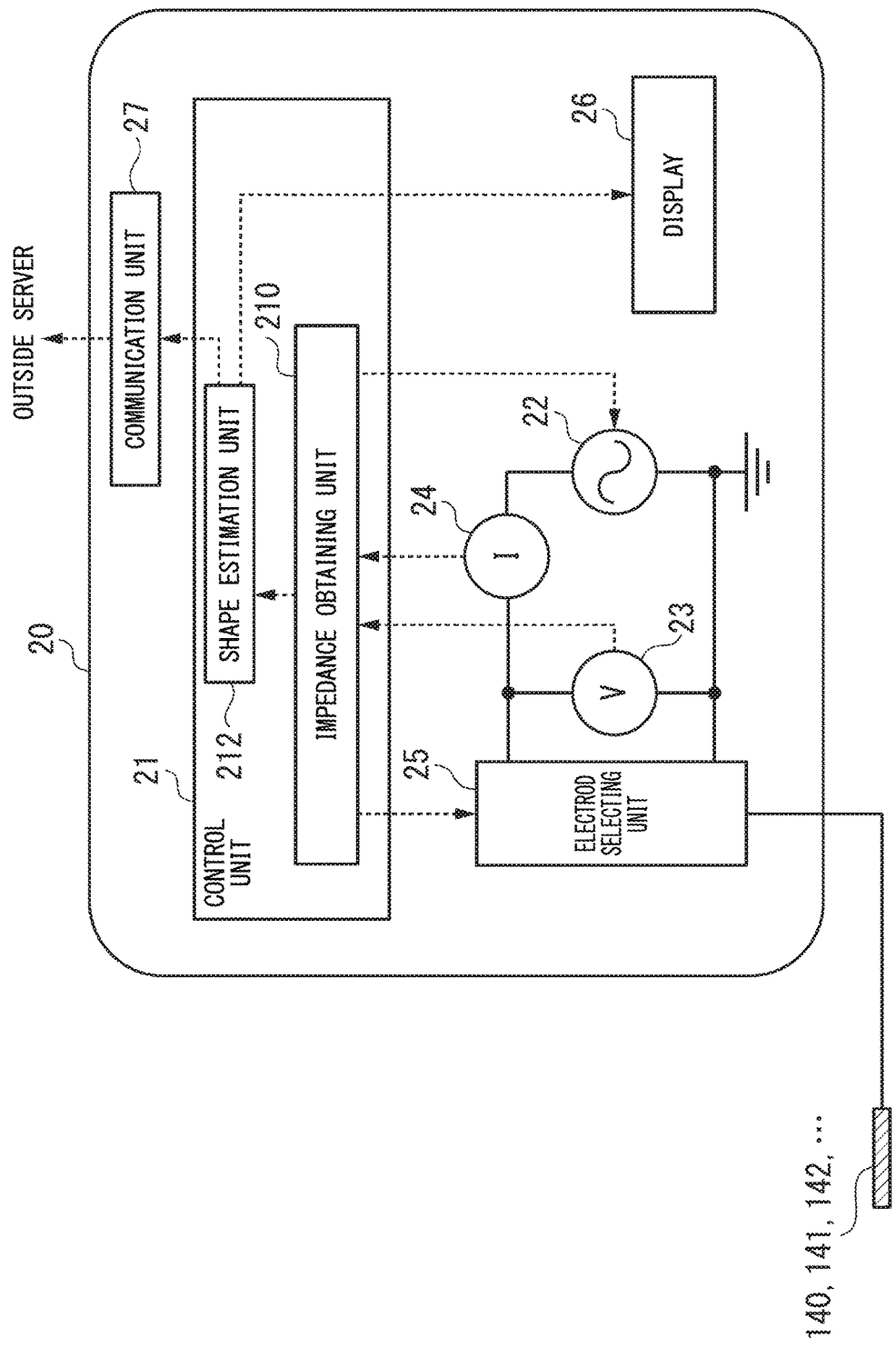
FIG. 17 is a diagram illustrating functional components of a shape estimation device.

FIG. 17 is a diagram illustrating functional components of a shape estimation device.

As shown in FIG. 17, the main unit 20 of the shape estimation device includes a tape portion which is used in a state of having a plurality of strain gauges 140, 141, . . . arrayed along a longitudinal direction and being wound around a measuring object, and a shape estimation unit 212 that estimates the shape of an area of the tape portion wound around the measuring object, based on the radius of curvature which is detected by the plurality of strain gauges 140, 141, . . . .

Meanwhile, the respective functional component of the shape estimation device shown in FIG. 17 are the same as the respective functional component (FIG. 4) corresponding to those of the length measurement device 1 according to each of the embodiments described above.

Figure 18:
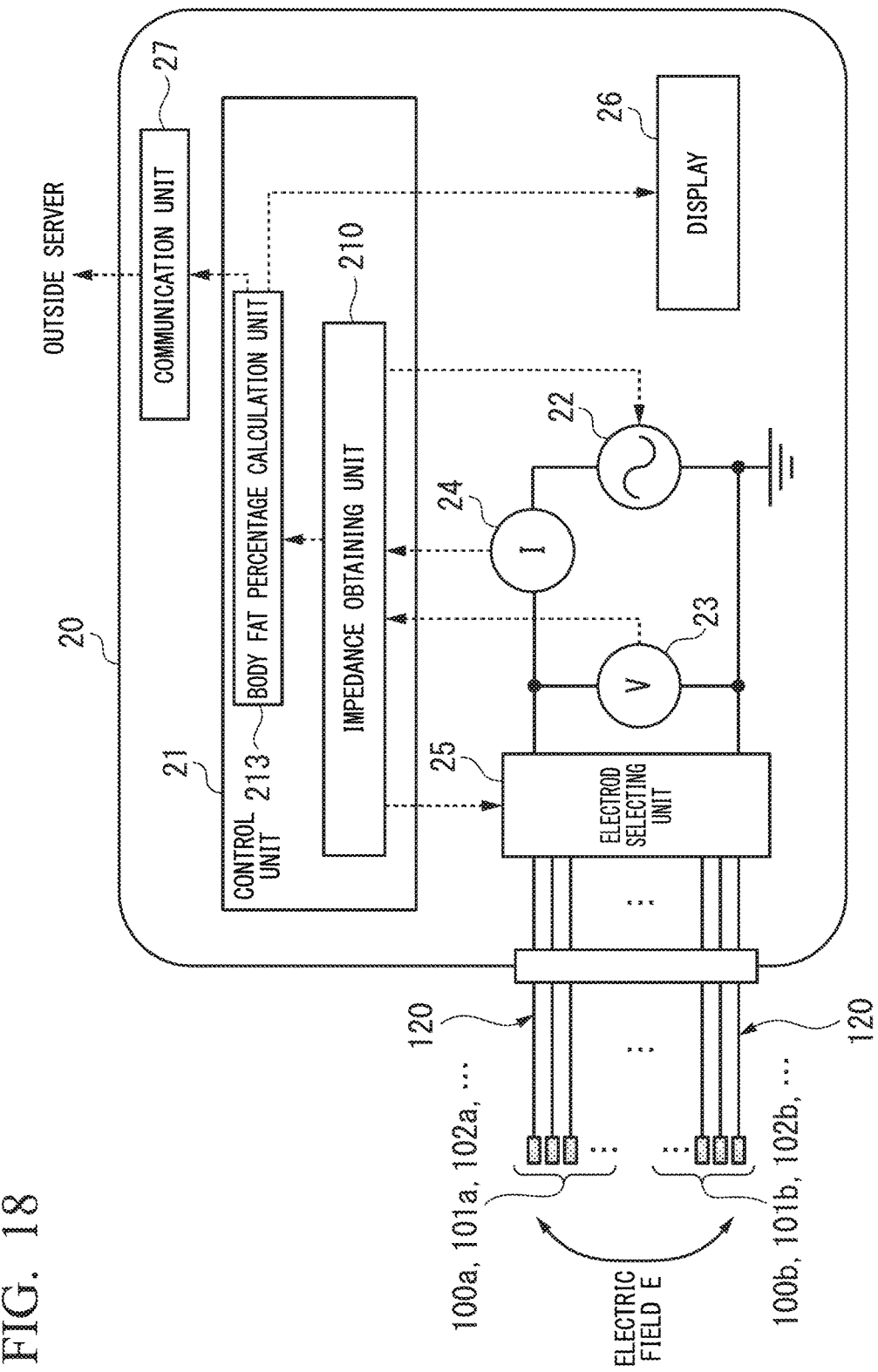
FIG. 18 is a diagram illustrating functional components of a body fat percentage measurement device.

FIG. 18 is a diagram illustrating functional components of a body fat percentage measurement device.

As shown in FIG. 18, the main unit 20 of the body fat percentage measurement device includes a tape portion which is used in a state of having a plurality of electrode pads 100a, 100b, . . . periodically arrayed along a longitudinal direction and being wound around a living body, an impedance acquisition unit 210 that selects a plurality of pairs of electrode pads from the plurality of electrode pads 100a, 100b, . . . and acquires electrical impedance therebetween for each of the plurality of pairs of electrode pads, and a body fat percentage calculation unit 213 that calculates the body fat percentage of a living body around which the tape portion is wound, based on the electrical impedance acquired by the impedance acquisition unit 210.

Meanwhile, the respective functional components of the body fat percentage measurement device shown in FIG. 18 are the same as the respective functional components corresponding to those of the length measurement device 1 according to each of the embodiments described above (FIG. 4).

INDUSTRIAL APPLICABILITY

According to each of the above-described embodiments, it is possible to simply and more accurately make a diagnosis of various objects to be measured which have different shapes or sizes of profiles.

REFERENCE SIGNS LIST

1: length measurement device
10: tape portion
100: signal wiring portion
111, 112: shield portion
113: insulating layer
100a, 100b, . . . , 10na, 10nb: electrode pad
11: flexible substrate
12: coated portion
120: routing wiring
13: connector
140, 141, . . . , 14m: strain gauge
20: main unit
21: control unit
210: impedance acquisition unit
211: length calculation unit
212: shape estimation unit
213: body fat percentage calculation unit
22: oscillation source
23: voltmeter
24: ammeter
25: electrode selecting unit
26: display
27: communication unit

The invention claimed is:

1. A length measurement device comprising:
a tape portion which is provided with a plurality of electrode pads arrayed along a longitudinal direction and is configured to be used in a state being wound around a measuring object;
an impedance acquisition unit configured to select any pair of electrode pads from the plurality of electrode pads and acquire electrical impedance between the pair of electrode pads;
a length calculation unit configured to calculate a length between the pair of electrode pads, based on a change in impedance of the pair of electrode pads; and
a positional relationship data storage unit configured to store positional relationship data indicating a positional relationship between the plurality of electrode pads,
wherein the length calculation unit configured to calculate the length between the pair of electrode pads, using the positional relationship data,
wherein the impedance acquisition unit is configured to select a plurality of the pairs of electrode pads and acquire electrical impedance therebetween for each of the pairs of electrode pads,
wherein the length calculation unit is configured to identify an area of the tape portion in which a pair of electrode pads having the electrical impedance set to be below a determination threshold are arrayed, and calculate a length of the identified area,
wherein the impedance acquisition unit is further configured to perform a first acquiring step of selecting a plurality of pairs of electrode pads arrayed at a first separation distance and acquiring electrical impedance therebetween for each of the plurality of pairs of electrode pads, and a second acquiring step of selecting a plurality of pairs of electrode pads arrayed at a second separation distance larger than the first separation distance and acquiring electrical impedance therebetween for each of the plurality of pairs of electrode pads, and
wherein in a case where a plurality of proximity areas which are areas of the tape portion having the electrical impedance, acquired in the first acquiring step, set to be below the determination threshold exist with a non-proximity area which is an area exceeding the determination threshold interposed therebetween, the length calculation unit determines whether the electrical impedance acquired in the second acquiring step is below the determination threshold in the non-proximity area, and calculates a length of an entire area in which the plurality of proximity areas exist in a case where the electrical impedance is set to be below the determination threshold.

2. The length measurement device according to claim 1, wherein the tape portion is formed by arraying the plurality of electrode pads on a flexible substrate.

3. The length measurement device according to claim 1, wherein the length calculation unit is configured to calculate the length in a case where the electrical impedance is set to be above a determination threshold or set to be below the determination threshold.

4. The length measurement device according to claim 1, wherein the tape portion is coated by a coated portion of which a surface is formed of an insulator.

5. The length measurement device according to claim 4, wherein the tape portion further includes a shield portion constituted by a conductor formed inside the coated portion so as to cover any one surface of the plurality of electrode pads and both surfaces of a routing wiring connected to the electrode pad.

6. The length measurement device according to claim 1, wherein the tape portion is configured such that the electrode pad and a routing wiring connected thereto are formed of a conductive fiber.

7. The length measurement device according to claim 1, wherein the tape portion further includes a shape estimation unit that has a plurality of curvature sensors arrayed along a longitudinal direction, and is configured to estimate a shape of an area of the tape portion which is wound around the measuring object, based on a radius of curvature which is detected by the plurality of curvature sensors.

8. The length measurement device according to claim 7, wherein each of the plurality of curvature sensors is provided integrally with each of the plurality of electrode pads.

9. The length measurement device according to claim 1, further comprising a body fat percentage calculation unit configured to calculate a body fat percentage of a living body around which the tape portion is wound, based on the electrical impedance acquired by the impedance acquisition unit.

10. A length measurement device comprising:
    a tape portion which is provided with a plurality of electrode pads periodically arrayed along a longitudinal direction and is configured to be used in a state being wound around a measuring object;
    an impedance acquisition unit configured to select a plurality of pairs of electrode pads from the plurality of electrode pads and acquire electrical impedance therebetween for each of the plurality of pairs of electrode pads; and
    a length calculation unit configured to identify an area of the tape portion in which a pair of electrode pads having the electrical impedance set to be below a determination threshold are arrayed, and calculate a length of the identified area,
    wherein the impedance acquisition unit is further configured to perform a first acquiring step of selecting a plurality of pairs of electrode pads arrayed at a first separation distance and acquiring electrical impedance therebetween for each of the plurality of pairs of electrode pads, and a second acquiring step of selecting a plurality of pairs of electrode pads arrayed at a second separation distance larger than the first separation distance and acquiring electrical impedance therebetween for each of the plurality of pairs of electrode pads, and
    wherein in a case where a plurality of proximity areas which are areas of the tape portion having the electrical impedance, acquired in the first acquiring step, set to be below the determination threshold exist with a non-proximity area which is an area exceeding the determination threshold interposed therebetween, the length calculation unit determines whether the electrical impedance acquired in the second acquiring step is below the determination threshold in the non-proximity area, and calculates a length of an entire area in which the plurality of proximity areas exist in a case where the electrical impedance is set to be below the determination threshold.

* * * * *